US012791560B2

(12) United States Patent
Bodenmiller et al.

(10) Patent No.: US 12,791,560 B2
(45) Date of Patent: Nov. 10, 2026

(54) METHOD FOR DETERMINING THE LIKELIHOOD OF A PATIENT BEING RESPONSIVE TO CANCER IMMUNOTHERAPY

(71) Applicant: UNIVERSITÄT ZÜRICH, Zürich (CH)

(72) Inventors: Bernd Bodenmiller, Zürich (CH); Johanna Wagner, Zürich (CH); Stephane Chevrier, Zürich (CH)

(73) Assignee: UNIVERSITÄT ZÜRICH, Zurich (CH)

(*) Notice: Subject to any disclaimer, the term of this patent is extended or adjusted under 35 U.S.C. 154(b) by 1315 days.

(21) Appl. No.: 17/602,757

(22) PCT Filed: Mar. 20, 2020

(86) PCT No.: PCT/EP2020/057893

§ 371 (c)(1),
(2) Date: Oct. 10, 2021

(87) PCT Pub. No.: WO2020/207771

PCT Pub. Date: Oct. 15, 2020

(65) Prior Publication Data

US 2022/0178926 A1 Jun. 9, 2022

(30) Foreign Application Priority Data

Apr. 10, 2019 (EP) .................................... 19168471

(51) Int. Cl.
*G01N 33/57515* (2026.01)
*G01N 33/575* (2026.01)

(52) U.S. Cl.
CPC ... *G01N 33/57515* (2026.01); *G01N 33/5759* (2026.01)

(58) Field of Classification Search
None
See application file for complete search history.

(56) References Cited

U.S. PATENT DOCUMENTS

2009/0312437 A1* 12/2009 Cohen ..................... A61P 15/12 435/375
2019/0263912 A1* 8/2019 Haber ................ C07K 16/2833

FOREIGN PATENT DOCUMENTS

| | | |
|---|---|---|
| WO | 2015117164 | 8/2015 |
| WO | 2016109546 | 7/2016 |
| WO | 2018147291 | 8/2018 |

OTHER PUBLICATIONS

Lacombe et al., Flow cytometry CD45 gating for immunophenotyping of acute myeloid leukemia, Leukemia, Nov. 1997, pp. 1878-1886. (Year: 1997).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Chen et al., The positivity of estrogen receptor and progesterone receptor may not be associated with metastasis and recurrence in epithelial ovarian cancer, Scientific Reports 7: 16933, Dec. 2017, pp. 1-7 (Year: 2017).*
Chan et al., Changes of tumor infiltrating lymphocyte subtypes before and after neoadjuvant endocrine therapy in estrogen receptor-positive breast cancer patients, Int J Biol Markers 2012, 27(4), pp. e295-e304/ (Year: 2012).*
Jenks et al., CD4:CD8 ratio and CD8+ cell count for prognostiicaling mortality in HIV-infected patients on antiretroviral therapy, J Lab Precis Med. Feb. 3, 2018; pp. 1-4. (Year: 2018).*
Eisenstein et al "cellular censuses to guide cancer care", Nature, macmillan journals LTD, London, vol. 567, No. 7749, Mar. 26, 2019, pp. 555-557.

* cited by examiner

*Primary Examiner* — Gary Counts
(74) *Attorney, Agent, or Firm* — JMB Davis Ben-David

(57) ABSTRACT

Described herein is a method for determining the likelihood of a patient being responsive to cancer immunotherapy by determining the amount of T cells expressing the markers PD-1, CTLA-4, TIM-3, and CD38 and the amount of regulatory T cells (T-regs).

18 Claims, 15 Drawing Sheets

A

METHOD FOR DETERMINING THE LIKELIHOOD OF A PATIENT BEING RESPONSIVE TO CANCER IMMUNOTHERAPY

CROSS-REFERENCE TO RELATED APPLICATIONS

This is the U.S. National Stage of International Patent Application No. PCT/EP2020/057893 filed on Mar. 20, 2020, which in turn claims the benefit of European Patent Application No. 19168471.1 filed on Apr. 10, 2019.

The present invention relates to a method for determining the likelihood of a patient being responsive to cancer immunotherapy by determining the amount of T cells expressing the markers PD-1, CTLA-4, TIM-3, and CD38 and the amount of regulatory T cells (T-regs).

BACKGROUND OF THE INVENTION

Breast cancer is the major cause of cancer death among women worldwide. A major obstacle for implementation of precision medicine is our lack of understanding the breast cancer ecosystem. Tumor ecosystems are comprised of cancer cells, infiltrating immune cells, stromal cells, and other cell types together with non-cellular tissue components. Cancer cells and tumor-associated cells are phenotypically and functionally heterogeneous due to genetic and non-genetic sources. Targets of current therapies and therapies under development, including ER, HER2, PI3K, AKT, mTOR, AR, EGFR, PARP, BCL-2, Survivin, CDK4/6, and methyltransferases, are heterogeneously expressed within and between patients. This heterogeneity equips cancer cells for proliferation, survival, and invasion and likely underlies differential treatment efficacies. Recent single-cell genomics and transcriptomics analyses provided insights into intratumor genomic diversity and intertumor differences in clonal composition, but very few cells and tumors were analyzed. In the healthy mammary gland, phenotypes of normal luminal and myoepithelial (basal) cells are tightly controlled. Luminal cells heterogeneously express ER, PR, and cytokeratins K7, K8, and K18, while basal cells express K5, K14, and SMA for proper tissue function.

Tumor ecosystems are further shaped by cellular relationships, and strategies targeting relationships that promote tumor development hold considerable promise. Examples are immune checkpoint inhibition therapies targeting exhausted and regulatory T cells (T-regs). T cell exhaustion can be mediated by tumor cells, tumor-associated macrophages (TAMs), and stromal cells through activation of the co-inhibitory receptors PD-1, CTLA-4, and TIM-3. T-regs can secrete immunosuppressive cytokines. Ongoing clinical trials suggest that the response rates to checkpoint inhibition therapies in breast cancer are not comparable to those of melanoma or lung cancer patients, likely due to lower immunogenicity. However, in cohorts selected for patients with PD-L1$^+$ breast tumors, higher overall response rates were reported. TAMs can modulate tumor ecosystems either through immunosuppressive actions (e.g., PD-L1 expression) or by promoting tumor growth, angiogenesis, and invasion and are thus promising therapeutic targets.

Given the heterogeneity of cell phenotypes and cellular relationships in breast cancer, patient classification and treatment should ideally consider the entire cancer ecosystem. Recent single-cell RNA sequencing studies provided a glimpse into breast cancer immune cell phenotypic diversity, laying a foundation for studies using large patient cohorts. Currently, however, breast tumors are stratified for clinical purposes based on tumor cell expression of ER, PR, HER2, and the proliferation marker Ki-67. These biomarkers serve as surrogates for prognostic gene expression profiles and categorize tumors as Luminal A (ER$^+$ and/or PR$^+$, HER2$^-$, Ki-67$^+$ <20%), Luminal B (ER$^+$ and/or PR$^+$, HER2$^-$, Ki-67$^+$ ≥20%), Luminal B-HER2$^+$ (ER$^+$ and/or PR$^+$, HER2$^+$), HER2$^+$ (ER-PR-HER2$^+$), and triple-negative (TN; ER-PR-HER2-). Alternative classification schemes based on gene expression and genomic alterations were proposed. In addition, pathological tumor grading assesses morphological deviation of tumor tissue and cells from normal to predict patient prognosis. Although these stratifications have improved therapy success, patient responses vary within each subtype, demanding a better characterization of breast cancer ecosystems.

Based on the above-mentioned state of the art, the objective of the present invention is to provide means and methods to determine the likelihood of a patient being responsive to cancer immunotherapy. This objective is attained by the subject-matter of the independent claims of the present specification.

SUMMARY OF THE INVENTION

A first aspect of the invention relates to a method of determining a likelihood of an ER-positive cancer patient being responsive to cancer immunotherapy by identification of certain immune cell subtypes. The cancer immunotherapy comprises administration of a checkpoint modulator agent.

An alternative aspect of the present invention relates to a system facilitating the detection of the immune cell subtypes indicative of a patient's responsiveness to cancer immunotherapy.

A second aspect of the invention relates to a checkpoint modulator agent for treatment of ER-positive cancer, in a patient assigned a high likelihood of being responsive to the treatment by a method according to the first aspect. This aspect might also be formulated as a method of treatment of a cancer patient, the method comprising the detection of certain immune cell subtypes as taught herein.

DETAILED DESCRIPTION OF THE INVENTION

Terms and Definitions

Figure 1:
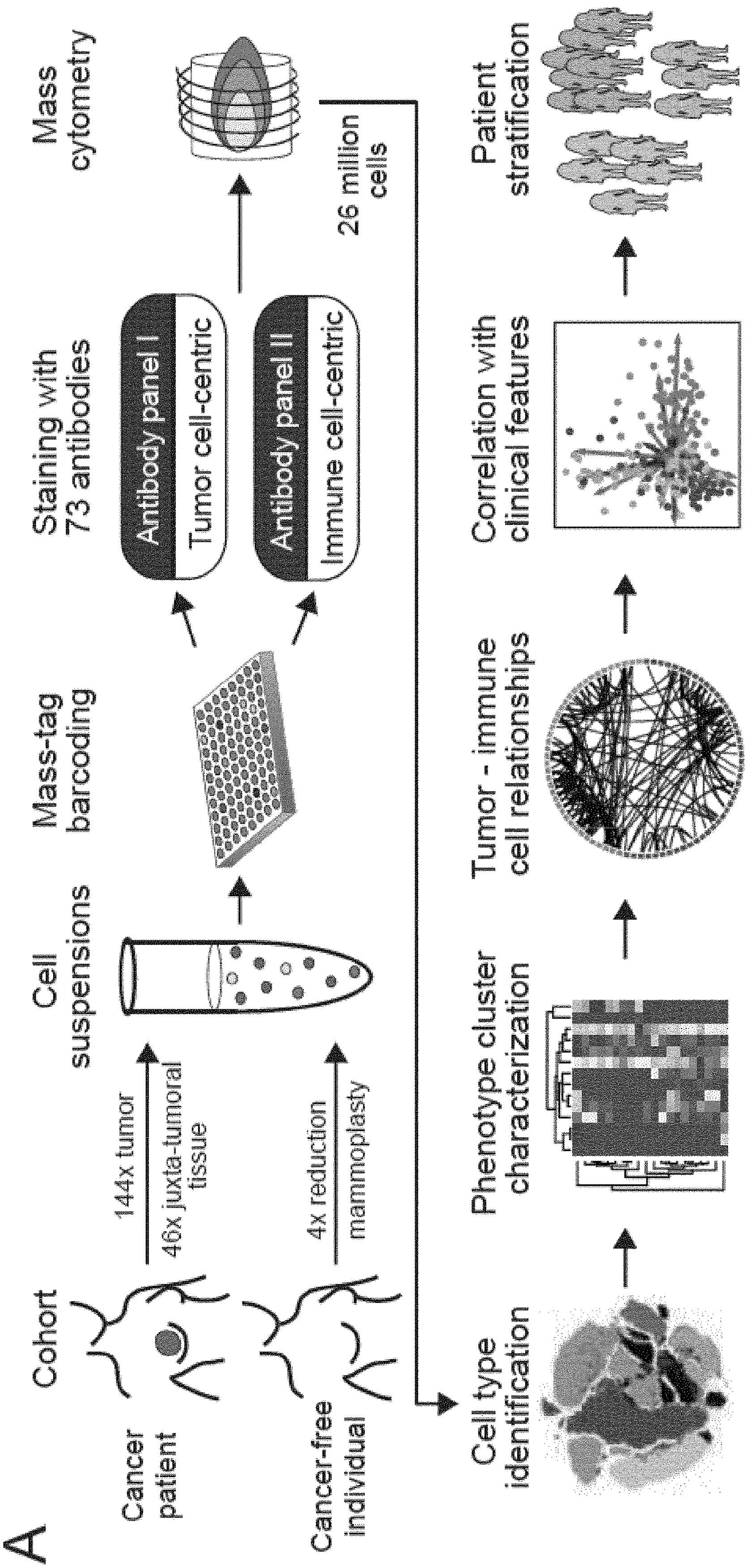
FIG. 1 A single-cell proteomic atlas of breast cancer ecosystems.
Figure 1:
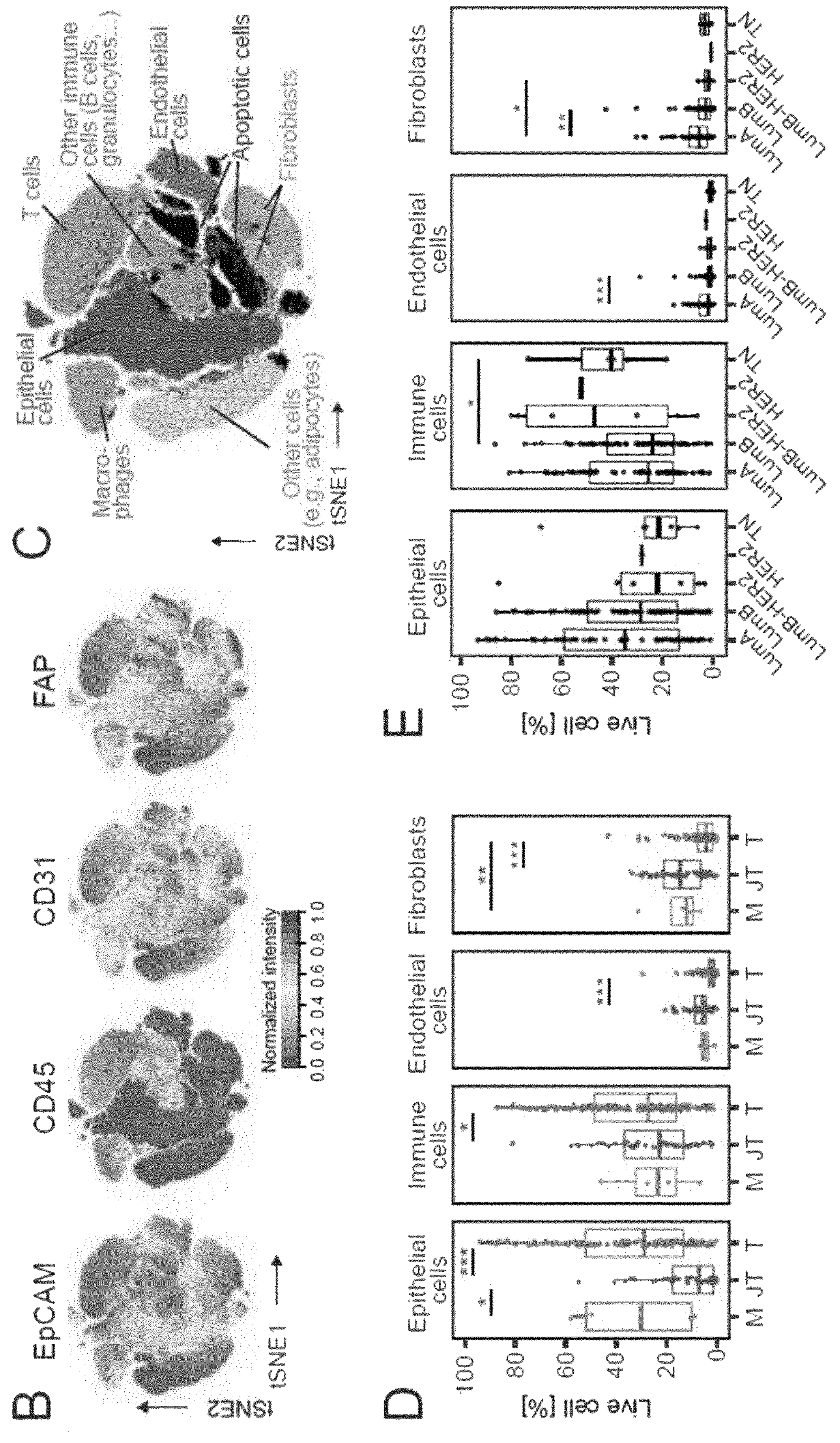
Figure 1:
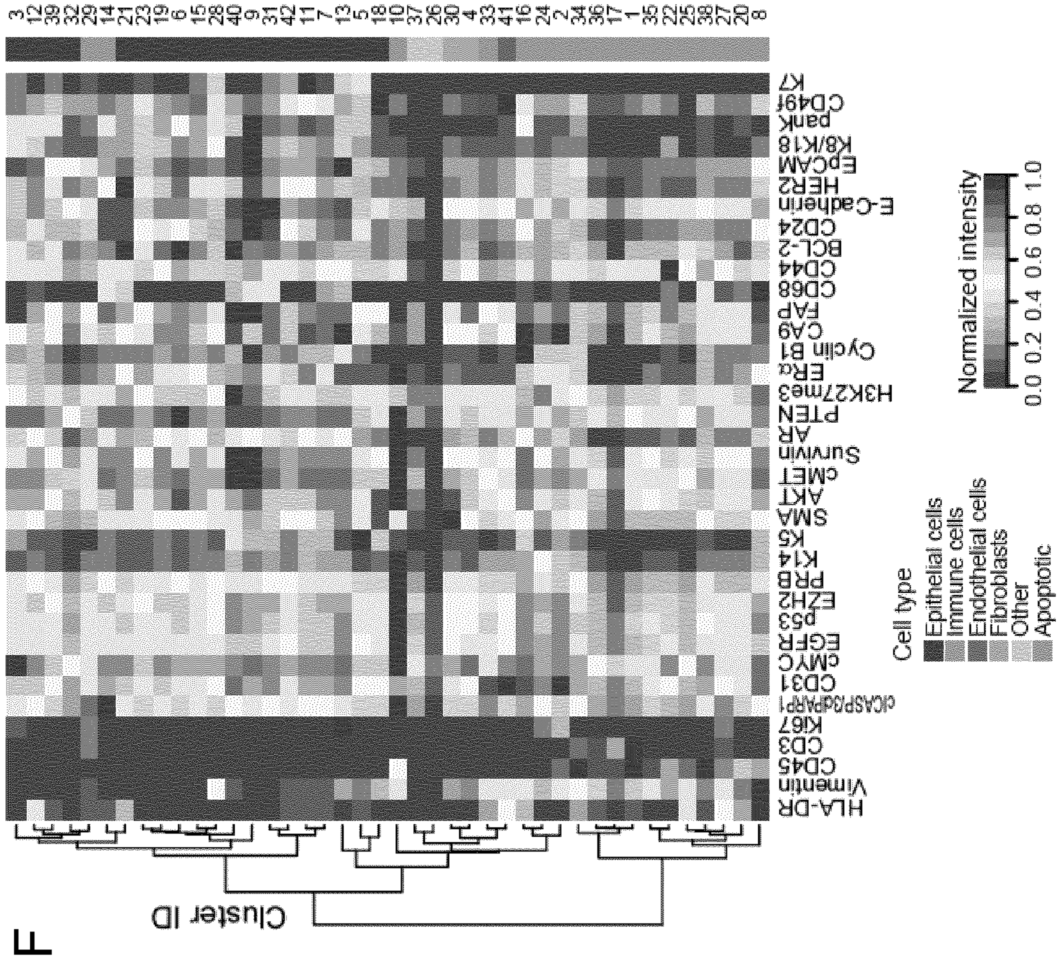

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.) and chemical methods.

In the present specification, the term positive, when used in the context of expression of a marker, refers to expression of an antigen assayed by a fluorescently labelled antibody, wherein the label's fluorescence on the structure (for example, a cell) referred to as "positive" is at least 30% higher (≥30%), particularly ≥50% or ≥80%, in median fluorescence intensity in comparison to staining with an isotype-matched fluorescently labelled antibody which does not specifically bind to the same target. Such expression of a marker is indicated by a superscript "plus" ($^{+}$), following the name of the marker, e.g. $CD4^{+}$.

In the present specification, the term negative, when used in the context of expression of a marker, refers to expression of an antigen assayed by a fluorescently labelled antibody, wherein the median fluorescence intensity is less than 30% higher, particularly less than 15% higher, than the median fluorescence intensity of an isotype-matched antibody which does not specifically bind the same target. Such expression of a marker is indicated by a superscript minus ($^{-}$), following the name of the marker, e.g. $CD127^{-}$.

High expression of a marker, for example high expression of CD38, refers to the expression level of such marker in a clearly distinguishable cell population that is detected by FACS showing the highest fluorescence intensity per cell compared to the other populations characterized by a lower fluorescence intensity per cell or by mass cytometry. A high expression is indicated by superscript "high" or "hi" following the name of the marker, e.g. $CD38^{high}$. The term "is expressed highly" refers to the same feature.

Low expression of a marker, for example low expression of CD38, refers to the expression level of such marker in a clearly distinguishable cell population that is detected by FACS showing the lowest fluorescence intensity per cell compared to the other populations characterized by higher fluorescence intensity per cell or by mass cytometry. A low expression is indicated by superscript "low" or "lo" following the name of the marker, e.g. $CD38^{low}$. The term "is expressed lowly" refers to the same feature.

The expression of a marker may be assayed via techniques such as fluorescence microscopy, flow cytometry, ELISPOT, ELISA, multiplex analyses or by mass cytometry.

Surface molecule expression may also be assessed by adding detection antibodies to stimulation cultures e.g.: CD154 and CD137. In case CD154 is used, CD154 detection antibody may be added to culture at stimulation initiation or after stimulation. In the latter case, an antibody against CD40 may be added to facilitate CD154 detection.

In the context of the present specification, the term mass cytometry relates to a mass spectrometry technique, wherein antibodies are conjugated with isotopically pure elements and these antibodies bind to cellular proteins. Cells are nebulized and sent through an argon plasma, which ionizes the metal-conjugated antibodies. A time-of-flight mass spectrometer is then used to detect the metal signals.

As used herein, expression refers to the process by which DNA is transcribed into mRNA and/or the process by which the transcribed mRNA is subsequently translated into peptides, polypeptides or proteins. If the polynucleotide is derived from genomic DNA, expression may include splicing of the mRNA in a eukaryotic cell. Expression may be assayed both on the level of transcription and translation, in other words mRNA and/or protein product.

In the context of the present specification, the term checkpoint inhibitory agent or checkpoint inhibitory antibody is meant to encompass an agent, particularly an antibody (or antibody-like molecule) capable of disrupting the signal cascade leading to T cell inhibition after T cell activation as part of what is known in the art the immune checkpoint mechanism. Non-limiting examples of a checkpoint inhibitory agent or checkpoint inhibitory antibody include antibodies to CTLA-4 (Uniprot P16410), PD-1 (Uniprot Q15116), PD-L1 (Uniprot Q9NZQ7), B7H3 (CD276; Uniprot Q5ZPR3), TIM-3 (Uniprot Q8TDQ0), Gal9, VISTA, or Lag3.

In the context of the present specification, the term checkpoint agonist agent or checkpoint agonist antibody is meant to encompass an agent, particularly but not limited to an antibody (or antibody-like molecule) capable of engaging the signal cascade leading to T cell activation as part of what is known in the art the immune checkpoint mechanism. Non-limiting examples of receptors known to stimulate T cell activation include CD122 and CD137 (4-1BB; Uniprot Q07011). The term checkpoint agonist agent or checkpoint agonist antibody encompasses agonist antibodies to CD137 (4-1BB), CD134 (OX40), CD357 (GITR), CD278 (ICOS), CD27, or CD28.

In the context of the present specification, the term (immune) checkpoint modulatory agent encompasses checkpoint inhibitory agents, checkpoint inhibitory antibodies, checkpoint agonist agents and checkpoint agonist antibodies. Checkpoint inhibitory agents checkpoint agonist agents encompass also small molecules which intervene with the checkpoint signaling cascade.

In the context of the present specification, the term "a non-agonist CTLA-4 ligand" relates to a molecule that binds selectively to CTLA-4 under conditions prevailing in peripheral blood, without triggering the biological effect of CTLA-4 interaction with any of the physiological ligands of CTLA-4, particularly CD80 and/or CD86. This can also be referred to as "a neutralizing CTLA-4 ligand".

In the context of the present specification, the term "a non-agonist PD-1 ligand" relates to a molecule that binds selectively to PD-1 under conditions prevailing in peripheral blood, without triggering the biological effect of PD-1 interaction with any of the physiological ligands of PD-1, particularly PD-L1 or PD-L2. This can also be referred to as "a neutralizing PD-1 ligand".

A non-agonist PD-L1 (PD-L2) ligand is a molecule that binds selectively to PD-L1 (or to PD-L2) under conditions prevailing in peripheral blood, without triggering the biological effect of PD-L1 (PD-L2) interaction with any of its physiological ligands, particularly PD-1. This can also be referred to as "a neutralizing PD-L1 ligand".

Similarly, in the context of the present specification, the terms "a non-agonist LAG-3, TIM-3, BLTA, TIGIT, VISTA or B7/H3 ligand", such as a polypeptide ligand, relate to a molecule that binds selectively to LAG-3, TIM-3, BLTA, TIGIT, VISTA or B7/H3 under conditions prevailing in peripheral blood, without triggering the biological effect of LAG-3, TIM-3, BLTA, TIGIT, VISTA or B7/H3 with any of the physiological ligands of LAG-3, TIM-3, BLTA, TIGIT, VISTA or B7/H3.

In the context of the present specification, the term antibody refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains interconnected by disulfide bonds. Each heavy chain is comprised of a heavy chain variable region ($V_H$) and a heavy chain constant region ($C_H$). The heavy chain constant region is comprised of three domains, $C_H1$, $C_H2$ and $C_H3$. Each light chain is comprised of a light chain variable region (abbreviated herein as $V_L$) and a light chain constant region ($C_L$). The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system. Similarly, the term encompasses a so-called nanobody or single domain antibody, an antibody fragment consisting of a single monomeric variable antibody domain.

In the context of the present specification, the term humanized antibody refers to an antibody originally produced by immune cells of a non-human species, the protein sequences of which have been modified to increase their similarity to antibody variants produced naturally in humans. The term humanized antibody as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term antibody-like molecule in the context of the present specification refers to a molecule capable of specific binding to another molecule or target with high affinity/a Kd≤10E-8 mol/I. An antibody-like molecule binds to its target similarly to the specific binding of an antibody. The term antibody-like molecule encompasses a repeat protein, such as a designed ankyrin repeat protein (Molecular Partners, Zurich), an engineered antibody mimetic proteins exhibiting highly specific and high-affinity target protein binding (see US2012142611, US2016250341, US2016075767 and US2015368302, all of which are incorporated herein by reference). The term antibody-like molecule further encompasses, but is not limited to, a polypeptide derived from armadillo repeat proteins, a polypeptide derived from leucine-rich repeat proteins and a polypeptide derived from tetratricopeptide repeat proteins.

The term antibody-like molecule further encompasses a specifically binding polypeptide derived from

- a protein A domain,
- fibronectin domain FN3,
- consensus fibronectin domains,
- a lipocalins (see Skerra, Biochim. Biophys. Acta 2000, 1482(1-2):337-50),
- a polypeptide derived from a Zinc finger protein (see Kwan et al. Structure 2003, 11(7):803-813),
- Src homology domain 2 (SH2) or Src homology domain 3 (SH3),
- a PDZ domain,
- gamma-crystallin,
- ubiquitin,
- a cysteine knot polypeptide or a knottin,
- cystatin,
- Sac7d,
- a triple helix coiled coil (also known as alphabodies),
- a Kunitz domain or a Kunitz-type protease inhibitor and
- a carbohydrate binding module 32-2.

In the context of the present specification, the term fragment crystallizable (Fc) region is used in its meaning known in the art of cell biology and immunology; it refers to a fraction of an antibody comprising two identical heavy chain fragments comprised of a $C_H2$ and a $C_H3$ domain, covalently linked by disulfide bonds.

The term specific binding in the context of the present invention refers to a property of ligands that bind to their target with a certain affinity and target specificity. The affinity of such a ligand is indicated by the dissociation constant of the ligand. A specifically reactive ligand has a dissociation constant of $\leq 10^{-7}$ mol/L when binding to its target, but a dissociation constant at least three orders of magnitude higher in its interaction with a molecule having a globally similar chemical composition as the target, but a different three-dimensional structure.

In the context of the present specification, the term dissociation constant ($K_D$) is used in its meaning known in the art of chemistry and physics; it refers to an equilibrium constant that measures the propensity of a complex composed of [mostly two] different components to dissociate reversibly into its constituent components. The complex can be e.g. an antibody-antigen complex AbAg composed of antibody Ab and antigen Ag. $K_D$ is expressed in molar concentration [mol/l] and corresponds to the concentration of [Ab] at which half of the binding sites of [Ag] are occupied, in other words, the concentration of unbound [Ab] equals the concentration of the [AbAg] complex. The dissociation constant can be calculated according to the following formula:

$$K_D = \frac{[Ab]*[Ag]}{[AbAg]}$$

[Ab]: Concentration of Antibody; [Ag]: Concentration of Antigen; [AbAg]: Concentration of Antibodyantigen Complex In the context of the present specification, the terms off-rate (Koff;[1/sec]) and on-rate (Kon; [1/sec*M]) are used in their meaning known in the art of chemistry and physics; they refer to a rate constant that measures the dissociation (Koff) or association (Kon) of 5 an antibody with its target antigen. Koff and Kon can be experimentally determined using methods well established in the art. A method for determining the Koff and Kon of an antibody employs surface plasmon resonance. This is the principle behind biosensor systems such as the Biacore® or the ProteOn® system. They can also be used to determine the dissociation constant KD by using the following formula:

$$K_D = \frac{[K_{off}]}{[K_{on}]}$$

As used herein, the term pharmaceutical composition refers to a compound of the invention, or a pharmaceutically acceptable salt thereof, together with at least one pharmaceutically acceptable carrier. In certain embodiments, the pharmaceutical composition according to the invention is provided in a form suitable for topical, parenteral or injectable administration.

As used herein, the term pharmaceutically acceptable carrier includes any solvents, dispersion media, coatings, surfactants, antioxidants, preservatives (for example, antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington: the Science and Practice of Pharmacy, ISBN 0857110624).

As used herein, the term treating or treatment of any disease or disorder (e.g. cancer) refers in one embodiment, to ameliorating the disease or disorder (e.g. slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. Methods for assessing treatment and/or prevention of disease are generally known in the art, unless specifically described hereinbelow.

DETAILED DESCRIPTION OF THE INVENTION

Estrogen receptor positive cancer cells can be targeted by current therapies, for example by anti-estrogen drugs. 30% of the patients receiving such therapy, however, become resistant and progress to metastatic cancer.

One therapeutic alternative may be cancer immunotherapy, i.e. treatment with so-called checkpoint modulators. Hormone receptor positive tumors currently have a rather low response rate in immunotherapy (compared to, for example, triple negative breast cancers). The method of the invention facilitates identification of those patients who are likely to respond.

The inventors surprisingly identified PD-1$^+$CTLA-4$^+$ CD38$^+$ Tim-3$^+$ T cells and other immune cell types that predict cancer immunotherapy responsivity.

A first aspect of the invention relates to a method of determining a likelihood of a patient being responsive to cancer immunotherapy. The cancer immunotherapy comprises administration of a checkpoint modulator agent. In certain embodiments, the patient has been diagnosed with estrogen receptor positive cancer. In certain embodiments, the patient has been diagnosed with breast cancer.

The method of determining a likelihood of a patient being responsive to cancer immunotherapy comprises the steps of

- identifying immune cells from a tumor sample obtained from said patient;
- determining the number of immune cells expressing a combination of markers selected from PD-1, CTLA-4, CD38, CD45, CD3, CD25, TIM-3, FOXP3, CD4, and CD8;
- assigning a high likelihood of the patient being responsive to cancer immunotherapy if at least one ratio is above a threshold.

In certain embodiments, the tumour sample obtained from the patient is segregated into single cells before the number of immune cells expressing certain markers is determined.

In certain embodiments, certain immune cells are isolated before the number of immune cells expressing certain markers is determined. Isolation of cells is performed e.g. by magnetic labeling or fluorescence activated cell sorting. In certain embodiments, single-cell RNA sequencing is performed for determining the number of immune cells expressing a combination of markers.

In certain embodiments, the tumour sample obtained from the patient is directly analyzed from formalin-fixed paraffin-embedded tissue or formaldehyde-fixed paraffin-embedded tissue. In certain embodiments, analysis is performed with Imaging Mass Cytometry, Serial fluorescence imaging or other multiplexed tissue imaging methods.

An alternative aspect of the present invention relates to a system facilitating the detection of the immune cell subtypes indicative of a patient's responsiveness to cancer immunotherapy.

Such system comprises a device for identifying cells based on markers expressed on their surface and made detectable by specific ligands capable of selectively binding to the markers. The ligands in turn can be detected by dye molecules, which are detectable by light (fluorescence emission) or by specific isotope markers in mass spectroscopy. The system will therefore need to comprise a separation and detection means, such as a fluorescence based cytometer and/or a mass spectrograph, and a computing means for processing the data received from the separation and detection means, as well as an output device or interface.

In certain embodiments, the threshold for assigning a high likelihood of the patient being responsive to cancer immunotherapy is at least 7% of CD45$^+$ immune cells are CD3$^+$ CD4$^+$CD25$^+$FOXP3$^+$ regulatory T cells. In certain embodiments, the threshold for assigning a high likelihood of the patient being responsive to cancer immunotherapy is at least 8% of CD45$^+$ immune cells are CD3$^+$CD4$^+$CD25$^+$FOXP3$^+$ regulatory T cells. In certain embodiments, the threshold for assigning a high likelihood of the patient being responsive to cancer immunotherapy is at least 9% of CD45$^+$ immune cells are CD3$^+$CD4$^+$CD25$^+$FOXP3$^+$ regulatory T cells.

In certain embodiments, the threshold for assigning a high likelihood of the patient being responsive to cancer immunotherapy is at least 7% of CD45$^+$ immune cells are CD3$^+$ CD4$^+$CD25$^+$FOXP3$^+$CTLA-4$^+$ regulatory T cells. In certain embodiments, the threshold for assigning a high likelihood of the patient being responsive to cancer immunotherapy is at least 8% of CD45$^+$ immune cells are CD3$^+$CD4$^+$CD25$^+$ FOXP3CTLA-4$^+$ regulatory T cells. In certain embodiments, the threshold for assigning a high likelihood of the patient being responsive to cancer immunotherapy is at least 9% of CD45$^+$ immune cells are CD3$^+$CD4$^+$CD25$^+$FOXP3$^+$ CTLA-4$^+$ regulatory T cells.

In certain embodiments, the threshold for assigning a high likelihood of the patient being responsive to cancer immunotherapy is at least 3% of CD45$^+$ immune cells are PD-1$^+$ CTLA-4$^+$TIM3$^-$CD38$^-$ T cells. In certain embodiments, the threshold for assigning a high likelihood of the patient being responsive to cancer immunotherapy is at least 4% of CD45$^+$ immune cells are PD-1$^+$CTLA-4$^+$TIM3$^-$CD38$^-$ T cells. In certain embodiments, the threshold for assigning a high likelihood of the patient being responsive to cancer immunotherapy is at least 5% of CD45$^+$ immune cells are PD-1$^+$ CTLA-4$^+$TIM3$^-$CD38$^-$ T cells.

In certain embodiments, the threshold for assigning a high likelihood of the patient being responsive to cancer immunotherapy is at least 0.1% of CD45$^+$ immune cells are PD-1$^+$CTLA-4$^+$TIM3$^+$CD38$^+$ T cells. In certain embodiments, the threshold for assigning a high likelihood of the patient being responsive to cancer immunotherapy is at least 0.2% of CD45$^+$ immune cells are PD-1$^+$CTLA-4$^+$TIM3$^+$ CD38$^+$ T cells. In certain embodiments, the threshold for assigning a high likelihood of the patient being responsive to cancer immunotherapy is at least 0.3% of CD45$^+$ immune cells are PD-1$^+$CTLA-4$^+$TIM3$^+$CD38$^+$ T cells.

In certain embodiments, the threshold for assigning a high likelihood of the patient being responsive to cancer immunotherapy is at least 22% of CD4$^+$ T cells are CD3$^+$CD4$^+$ CD25$^+$FOXP3$^+$ regulatory T cells. In certain embodiments, the threshold for assigning a high likelihood of the patient being responsive to cancer immunotherapy is at least 25% of CD4$^+$ T cells are CD3$^+$CD4$^+$CD25$^+$FOXP3$^+$ regulatory T cells. In certain embodiments, the threshold for assigning a high likelihood of the patient being responsive to cancer immunotherapy is at least 28% of $CD4^+$ T cells are $CD3^+CD4^+CD25^+FOXP3^+$ regulatory T cells.

In certain embodiments, the threshold for assigning a high likelihood of the patient being responsive to cancer immunotherapy is at least 22% of $CD4^+$ T cells are $CD3^+CD4^+CD25^+FOXP3^+CTLA\text{-}4^+$ regulatory T cells. In certain embodiments, the threshold for assigning a high likelihood of the patient being responsive to cancer immunotherapy is at least 25% of $CD4^+$ T cells are $CD3^+CD4^+CD25^+FOXP3^+CTLA\text{-}4^+$ regulatory T cells. In certain embodiments, the threshold for assigning a high likelihood of the patient being responsive to cancer immunotherapy is at least 28% of $CD4^+$ T cells are $CD3^+CD4^+CD25^+FOXP3^+CTLA\text{-}4^+$ regulatory T cells.

In certain embodiments, the threshold for assigning a high likelihood of the patient being responsive to cancer immunotherapy is at least 4% of $CD45^+$ immune cells are $PD\text{-}1^+CTLA\text{-}4^+CD38^+CD4^+$ T cells. In certain embodiments, the threshold for assigning a high likelihood of the patient being responsive to cancer immunotherapy is at least 5% of $CD45^+$ immune cells are $PD\text{-}1^+CTLA\text{-}4^+CD38^+CD4^+$ T cells. In certain embodiments, the threshold for assigning a high likelihood of the patient being responsive to cancer immunotherapy is at least 6% of $CD45^+$ immune cells are $PD\text{-}1^+CTLA\text{-}4^+CD38^+CD4^+$ T cells.

In certain embodiments, the threshold for assigning a high likelihood of the patient being responsive to cancer immunotherapy is at least 0.4% of $CD45^+$ immune cells are $PD\text{-}1CTLA\text{-}4^+CD38^+CD8^+$ T cells. In certain embodiments, the threshold for assigning a high likelihood of the patient being responsive to cancer immunotherapy is at least 0.5% of $CD45^+$ immune cells are $PD\text{-}1^+CTLA\text{-}4^+CD38^+CD8^+$ T cells. In certain embodiments, the threshold for assigning a high likelihood of the patient being responsive to cancer immunotherapy is at least 0.6% of $CD45^+$ immune cells are $PD\text{-}1^+CTLA\text{-}4^+CD38^+CD8^+$ T cells.

In certain embodiments, the threshold for assigning a high likelihood of the patient being responsive to cancer immunotherapy is at least 12% of $CD4^+$ T cells are $PD\text{-}1^+CTLA\text{-}4^+CD38^+CD4^+$ T cells. In certain embodiments, the threshold for assigning a high likelihood of the patient being responsive to cancer immunotherapy is at least 14% of $CD4^+$ T cells are $PD\text{-}1^+CTLA\text{-}4^+CD38^+CD4^+$ T cells. In certain embodiments, the threshold for assigning a high likelihood of the patient being responsive to cancer immunotherapy is at least 16% of $CD4^+$ T cells are $PD\text{-}1^+CTLA\text{-}4^+CD38^+CD4^+$ T cells.

In certain embodiments, the threshold for assigning a high likelihood of the patient being responsive to cancer immunotherapy is at least 23% of $CD8^+$ T cells are $PD\text{-}1^+CTLA\text{-}4^+CD38^+CD8^+$ T cells. In certain embodiments, the threshold for assigning a high likelihood of the patient being responsive to cancer immunotherapy is at least 25% of $CD8^+$ T cells are $PD\text{-}1^+CTLA\text{-}4^+CD38^+CD8^+$ T cells. In certain embodiments, the threshold for assigning a high likelihood of the patient being responsive to cancer immunotherapy is at least 27% of $CD8^+$ T cells are $PD\text{-}1^+CTLA\text{-}4^+CD38^+CD8^+$ T cells.

In certain embodiments, a high likelihood of the patient being responsive to cancer immunotherapy is assigned if at least two of the above-mentioned ratios are above said thresholds. In certain embodiments, a high likelihood of the patient being responsive to cancer immunotherapy is assigned if at least three of the above-mentioned ratios are above said thresholds. In certain embodiments, a high likelihood of the patient being responsive to cancer immunotherapy is assigned if at least four of the above-mentioned ratios are above said thresholds. In certain embodiments, a high likelihood of the patient being responsive to cancer immunotherapy is assigned if at least five of the above-mentioned ratios are above said thresholds. In certain embodiments, a high likelihood of the patient being responsive to cancer immunotherapy is assigned if at least six of the above-mentioned ratios are above said thresholds. In certain embodiments, a high likelihood of the patient being responsive to cancer immunotherapy is assigned if at least seven of the above-mentioned ratios are above said thresholds. In certain embodiments, a high likelihood of the patient being responsive to cancer immunotherapy is assigned if at least eight of the above-mentioned ratios are above said thresholds. In certain embodiments, a high likelihood of the patient being responsive to cancer immunotherapy is assigned if at least nine of the above-mentioned ratios are above said thresholds. In certain embodiments, a high likelihood of the patient being responsive to cancer immunotherapy is assigned if all of the above-mentioned ratios are above said thresholds.

The described markers indicate the extent of exhaustion of T cells. T cells are increasingly exhausted, and with increased exhaustion more and more co-inhibitory receptors are expressed. PD-1, CTLA-4, TIM3, and CD38 are markers for exhaustion of T cells.

In certain embodiments, the breast cancer is estrogen receptor positive breast cancer. In certain embodiments, the estrogen receptor positive cancer is breast cancer. In certain embodiments, the estrogen receptor positive cancer is ovarian cancer. In certain embodiments, the estrogen receptor positive cancer is endometrial cancer. In certain embodiments, the estrogen receptor positive cancer is cervical cancer. In certain embodiments, the estrogen receptor positive cancer is uterine cancer.

ER receptor positive breast cancer cells are those that measurably express estrogen receptor.

In certain embodiments, the markers selected from PD-1, CTLA-4, CD38, CD45, CD3, CD25, TIM-3, FOXP3, CD4, and CD8 are identified by mass cytometry.

In certain embodiments, the markers selected from PD-1, CTLA-4, CD38, CD45, CD3, CD25, TIM-3, FOXP3, CD4, and CD8 are identified by fluorescence cytometry.

A second aspect of the invention relates to a checkpoint modulator agent for treatment of ER-positive cancer, in a patient assigned a high likelihood of being responsive to the treatment by a method according to aspect one. In certain embodiments, the checkpoint modulator agent is for treatment of ER-positive breast cancer, in a patient assigned a high likelihood of being responsive to the treatment by a method according to aspect one.

In certain embodiments, the checkpoint modulator agent is applied for treatment of ER-positive cancer in a patient having a tumour wherein at least 7% of $CD45^+$ immune cells are $CD3^+CD4^+CD25^+FOXP3^+$ regulatory T cells. In certain embodiments, the checkpoint modulator agent is applied for treatment of ER-positive cancer in a patient having a tumour wherein at least 8% of $CD45^+$ immune cells are $CD3^+CD4^+CD25^+FOXP3^+$ regulatory T cells.

In certain embodiments, the checkpoint modulator agent is applied for treatment of ER-positive cancer in a patient having a tumour wherein at least 9% of $CD45^+$ immune cells are $CD3^+CD4^+CD25^+FOXP3^+$ regulatory T cells.

In certain embodiments, the checkpoint modulator agent is applied for treatment of ER-positive cancer in a patient having a tumour wherein at least 7% of $CD45^+$ immune cells are $CD3^+CD4^+CD25^+FOXP3^+CTLA\text{-}4^+$ regulatory T cells. In certain embodiments, the checkpoint modulator agent is applied for treatment of ER-positive cancer in a patient having a tumour wherein at least 8% of $CD45^+$ immune cells are $CD3^+CD4^+CD25^+FOXP3^+CTLA\text{-}4^+$ regulatory T cells. In certain embodiments, the checkpoint modulator agent is applied for treatment of ER-positive cancer in a patient having a tumour wherein at least 9% of $CD45^+$ immune cells are $CD3^+CD4^+CD25^+FOXP3^+CTLA\text{-}4^+$ regulatory T cells.

In certain embodiments, the checkpoint modulator agent is applied for treatment of ER-positive cancer in a patient having a tumour wherein at least 3% of $CD45^+$ immune cells are $PD\text{-}1^+CTLA\text{-}4^+TIM3^-CD38^-$ T cells. In certain embodiments, the checkpoint modulator agent is applied for treatment of ER-positive cancer in a patient having a tumour wherein at least 4% of $CD45^+$ immune cells are $PD\text{-}1^+CTLA\text{-}4^+TIM3^-CD38^-$ T cells. In certain embodiments, the checkpoint modulator agent is applied for treatment of ER-positive cancer in a patient having a tumour wherein at least 5% of $CD45^+$ immune cells are $PD\text{-}1CTLA\text{-}4^+TIM3^-CD38^-$ T cells.

In certain embodiments, the checkpoint modulator agent is applied for treatment of ER-positive cancer in a patient having a tumour wherein at least 0.1% of $CD45^+$ immune cells are $PD\text{-}1^+CTLA\text{-}4^+TIM3^+CD38^+$ T cells. In certain embodiments, the checkpoint modulator agent is applied for treatment of ER-positive cancer in a patient having a tumour wherein at least 0.2% of $CD45^+$ immune cells are $PD\text{-}1^+CTLA\text{-}4^+TIM3^+CD38^+$ T cells. In certain embodiments, the checkpoint modulator agent is applied for treatment of ER-positive cancer in a patient having a tumour wherein at least 0.3% of $CD45^+$ immune cells are $PD\text{-}1CTLA\text{-}4^+TIM3^+CD38^+$ T cells.

In certain embodiments, the checkpoint modulator agent is applied for treatment of ER-positive cancer in a patient having a tumour wherein at least 22% of $CD4^+$ T cells are $CD3^+CD4^+CD25^+FOXP3^+$ regulatory T cells. In certain embodiments, the checkpoint modulator agent is applied for treatment of ER-positive cancer in a patient having a tumour wherein at least 25% of $CD4^+$ T cells are $CD3^+CD4^+CD25^+FOXP3^+$ regulatory T cells. In certain embodiments, the checkpoint modulator agent is applied for treatment of ER-positive cancer in a patient having a tumour wherein at least 28% of $CD4^+$ T cells are $CD3^+CD4^+CD25^+FOXP3^+$ regulatory T cells.

In certain embodiments, the checkpoint modulator agent is applied for treatment of ER-positive cancer in a patient having a tumour wherein at least 22% of $CD4^+$ T cells are $CD3^+CD4^+CD25^+FOXP3^+CTLA\text{-}4^+$ regulatory T cells. In certain embodiments, the checkpoint modulator agent is applied for treatment of ER-positive cancer in a patient having a tumour wherein at least 25% of $CD4^+$ T cells are $CD3^+CD4^+CD25^+FOXP3^+CTLA\text{-}4^+$ regulatory T cells.

In certain embodiments, the checkpoint modulator agent is applied for treatment of ER-positive cancer in a patient having a tumour wherein at least 28% of $CD4^+$ T cells are $CD3^+CD4^+CD25^+FOXP3^+CTLA\text{-}4^+$ regulatory T cells.

In certain embodiments, the checkpoint modulator agent is applied for treatment of ER-positive cancer in a patient having a tumour wherein at least 4% of $CD45^+$ immune cells are $PD\text{-}1^+CTLA\text{-}4^+CD38^+CD4^+$ T cells. In certain embodiments, the checkpoint modulator agent is applied for treatment of ER-positive cancer in a patient having a tumour wherein at least 5% of $CD45^+$ immune cells are $PD\text{-}1^+CTLA\text{-}4^+CD38^+CD4^+$ T cells. In certain embodiments, the checkpoint modulator agent is applied for treatment of ER-positive cancer in a patient having a tumour wherein at least 6% of $CD45^+$ immune cells are $PD\text{-}1CTLA\text{-}4^+CD38^+CD4^+$ T cells.

In certain embodiments, the checkpoint modulator agent is applied for treatment of ER-positive cancer in a patient having a tumour wherein at least 0.4% of $CD45^+$ immune cells are $PD\text{-}1^+CTLA\text{-}4^+CD38^+CD8^+$ T cells. In certain embodiments, the checkpoint modulator agent is applied for treatment of ER-positive cancer in a patient having a tumour wherein at least 0.5% of $CD45^+$ immune cells are $PD\text{-}1^+CTLA\text{-}4^+CD38^+CD8^+$ T cells. In certain embodiments, the checkpoint modulator agent is applied for treatment of ER-positive cancer in a patient having a tumour wherein at least 0.6% of $CD45^+$ immune cells are $PD\text{-}1CTLA\text{-}4^+CD38^+CD8^+$ T cells.

In certain embodiments, the checkpoint modulator agent is applied for treatment of ER-positive cancer in a patient having a tumour wherein at least 12% of $CD4^+$ T cells are $PD\text{-}1^+CTLA\text{-}4^+CD38^+CD4^+$ T cells. In certain embodiments, the checkpoint modulator agent is applied for treatment of ER-positive cancer in a patient having a tumour wherein at least 14% of $CD4^+$ T cells are $PD\text{-}1^+CTLA\text{-}4^+CD38^+CD4^+$ T cells. In certain embodiments, the checkpoint modulator agent is applied for treatment of ER-positive cancer in a patient having a tumour wherein at least 16% of $CD4^+$ T cells are $PD\text{-}1CTLA\text{-}4^+CD38^+CD4^+$ T cells.

In certain embodiments, the checkpoint modulator agent is applied for treatment of ER-positive cancer in a patient having a tumour wherein at least 23% of $CD8^+$ T cells are $PD\text{-}1^+CTLA\text{-}4^+CD38^+CD8^+$ T cells. In certain embodiments, the checkpoint modulator agent is applied for treatment of ER-positive cancer in a patient having a tumour wherein at least 25% of $CD8^+$ T cells are $PD\text{-}1^+CTLA\text{-}4^+CD38^+CD8^+$ T cells. In certain embodiments, the checkpoint modulator agent is applied for treatment of ER-positive cancer in a patient having a tumour wherein at least 27% of $CD8^+$ T cells are $PD\text{-}1CTLA\text{-}4^+CD38^+CD8^+$ T cells.

In certain embodiments, the patient is additionally treated with an anti-estrogen drug.

In certain embodiments, the checkpoint modulator agent is selected from a non-agonist ligand, particularly a non-agonist antibody or antibody-like molecule, specifically reactive to any one of CTLA-4, PD-1, PD-L1, PD-L2, LAG-3, TIM-3, BLTA, TIGIT, VISTA or B7/H3

In certain embodiments, the checkpoint modulator agent is selected from an agonist ligand, particularly an agonist antibody or antibody-like molecule, specifically reactive to any one of CD137 (4-1BB), CD134 (OX40), CD357 (GITR), CD278 (ICOS), CD27, or CD28.

Checkpoint Modulator Agents

In some embodiments, said non-agonist (neutralizing) CTLA-4 ligand is a polypeptide binding to CTLA-4. In certain embodiments, the non-agonist CTLA-4 ligand is a molecule that is capable of binding to CTLA-4 with a dissociation constant of at least $10^{-7}$ $M^{-1}$, $10^{-8}$ $M^{-1}$ or $10^{-9}$ $M^{-1}$ and which inhibits the biological activity of its respective target.

In one embodiment, said non-agonist CTLA-4 ligand is a gamma immunoglobulin binding to CTLA-4, without triggering the physiological response of CTLA-4 interaction with its binding partners CD80 and/or CD86.

Non-limiting examples for a CTLA-4 ligand are the clinically approved antibodies tremelimumab (CAS 745013-59-6) and ipilimumab (CAS No. 477202-00-9; Yervoy).

In some embodiments, said non-agonist PD-1 ligand is a polypeptide binding to PD-1. In certain embodiments, the non-agonist (neutralizing) PD-1 ligand or a non-agonist PD-L1 (PD-L2) ligand in the sense of the invention refers to a molecule that is capable of binding to PD-1 (PD-L1, PD-L2) with a dissociation constant of at least $10^{-7}$ $M^{-1}$, $10^{-8}$ $M^{-1}$ or $10^{-9}$ $M^{-1}$ and which inhibits the biological activity of its respective target.

In some embodiments, said non-agonist PD-1 ligand is a gamma immunoglobulin binding to PD-1, without triggering the physiological response of PD-1 interaction with its binding partners PD-L1 and/or PD-L2.

In some embodiments, said non-agonist PD-L1 (PD-L2) ligand is a gamma immunoglobulin binding to PD-L1 (PD-L2), without triggering the physiological response of PD-1 interaction with its binding partners PD-L1 and/or PD-L2.

Non-limiting examples for a PD-1/PD-L1 or PD-L2 ligands are the antibodies MDX-1105/BMS-936559, MDX-1106/BMS-936558/ONO-4538, MK-3475/SCH 900475 or AMP-224 currently undergoing clinical development.

In certain embodiments, the immune checkpoint inhibitor agent is an inhibitor of interaction of programmed cell death protein 1 (PD-1) with its receptor PD-L1. In certain embodiments, the immune checkpoint inhibitor agent is selected from the clinically available antibody drugs nivolumab (Bristol-Myers Squibb; CAS No 946414-94-4), pembrolizumab (Merck Inc.; CAS No. 1374853-91-4), pidilizumab (CAS No. 1036730-42-3), atezolizumab (Roche AG; CAS No. 1380723-44-3), and Avelumab (Merck KGaA; CAS No. 1537032-82-8).

In certain embodiments, the checkpoint modulator agent is a non-agonist (neutralizing) ligand to LAG-3, TIM-3, BLTA, TIGIT, VISTA or B7/H3.

A non-agonist polypeptide ligand of any of the above embodiments may be an antibody, an antibody fragment, an antibody-like molecule or an oligopeptide, any of which binds to and thereby inhibits CTLA-4, PD-1 PD-L1 (PD-L2), LAG-3, TIM-3, BLTA, TIGIT, VISTA or B7/H3 respectively.

The antibody fragment reactive to one of CTLA-4, PD-1 PD-L1 (PD-L2), LAG-3, TIM-3, BLTA, TIGIT, VISTA or B7/H3 may be a Fab domain or an Fv domain of an antibody, or a single-chain antibody fragment, which is a fusion protein consisting of the variable regions of light and heavy chains of an antibody connected by a peptide linker. The checkpoint modulator agent may also be a single domain antibody reactive to one of CTLA-4, PD-1 PD-L1 (PD-L2), LAG-3, TIM-3, BLTA, TIGIT, VISTA or B7/H3, consisting of an isolated variable domain from a heavy or light chain. Additionally, an antibody may also be a heavy-chain antibody consisting of only heavy chains such as antibodies found in camelids. An antibody-like molecule may be a repeat protein, such as a designed ankyrin repeat protein (Molecular Partners, Zürich).

A non-agonist polypeptide ligand according to the above aspect of the invention may be a peptide derived from the recognition site of a physiological ligand of CTLA-4, PD-1 or PD-L1 or PD-L2. Such oligopeptide ligand competes with the physiological ligand for binding to CTLA-4, PD-1 or PD-L1 or PD-L2, respectively.

A non-agonist polypeptide ligand according to the above aspect of the invention may also be a peptide derived from the recognition site of a physiological ligand of LAG-3, TIM-3, BLTA, TIGIT, VISTA or B7/H3. Such oligopeptide ligand competes with the physiological ligand for binding to LAG-3, TIM-3, BLTA, TIGIT, VISTA or B7/H3. Particularly, a non-agonist CTLA-4 ligand or non-agonist PD-1 ligand or non-agonist PD-L1 ligand or non-agonist PD-L2 ligand does not lead to attenuated T cell activity when binding to CTLA-4, PD-1, PD-L1 or PD-L2, respectively, on the surface on a T-cell. In certain embodiments, the term "non-agonist CTLA-4 ligand" or "non-agonist PD-1 ligand" covers both antagonists of CTLA-4 or PD-1 and ligands that are neutral vis-à-vis CTLA-4 or PD-1 signalling. In some embodiments, non-agonist CTLA-4 ligands used in the present invention are able, when bound to CTLA-4, to sterically block interaction of CTLA-4 with its binding partners CD80 and/or CD86 and non-agonist PD-1 ligands used in the present invention are able, when bound to PD-1, to sterically block interaction of PD-1 with its binding partners PD-L1 and/or PD-L2.

The term "gamma immunoglobulin" in this context is intended to encompass both complete immunoglobulin molecules and functional fragments thereof, wherein the function is binding to CTLA-4, PD-1 or PD-L1 (PD-L2) as laid out above.

Similarly, a dosage form for the prevention or treatment of cancer is provided, comprising a non-agonist ligand according to any of the above aspects or embodiments of the invention, administered to a patient identified of being receptive to checkpoint modulator therapy by the method of the invention.

Wherever alternatives for single separable features such as, for example, a diagnostic method or medical indication are laid out herein as "embodiments", it is to be understood that such alternatives may be combined freely to form discrete embodiments of the invention disclosed herein. Thus, any of the alternative embodiments for a medical indication may be combined with any diagnostic method mentioned herein.

The invention is further illustrated by the following examples and figures, from which further embodiments and advantages can be drawn. These examples are meant to illustrate the invention but not to limit its scope.

DESCRIPTION OF THE FIGURES

FIG. 1 A single-cell proteomic atlas of breast cancer ecosystems. (A) Experimental approach. (B) t-SNE plots of EpCAM, CD45, CD31, and FAP expression in 58,000 cells from all samples using a 0 to 1 normalization. (C) t-SNE as in B) colored by cell type. (D and E) Frequencies of live epithelial cells, immune cells, endothelial cells, and fibroblasts for D) mammoplasty (M), juxta-tumoral (JT), and tumor (T) samples and E) tumor subtypes. Wilcoxon rank-sum test was used for statistical analysis. * $p<0.05$,  $p<0.01$, * $p<0.001$. (F) Heatmap showing normalized marker expression for the cell-type PhenoGraph clusters.

Figure 2:
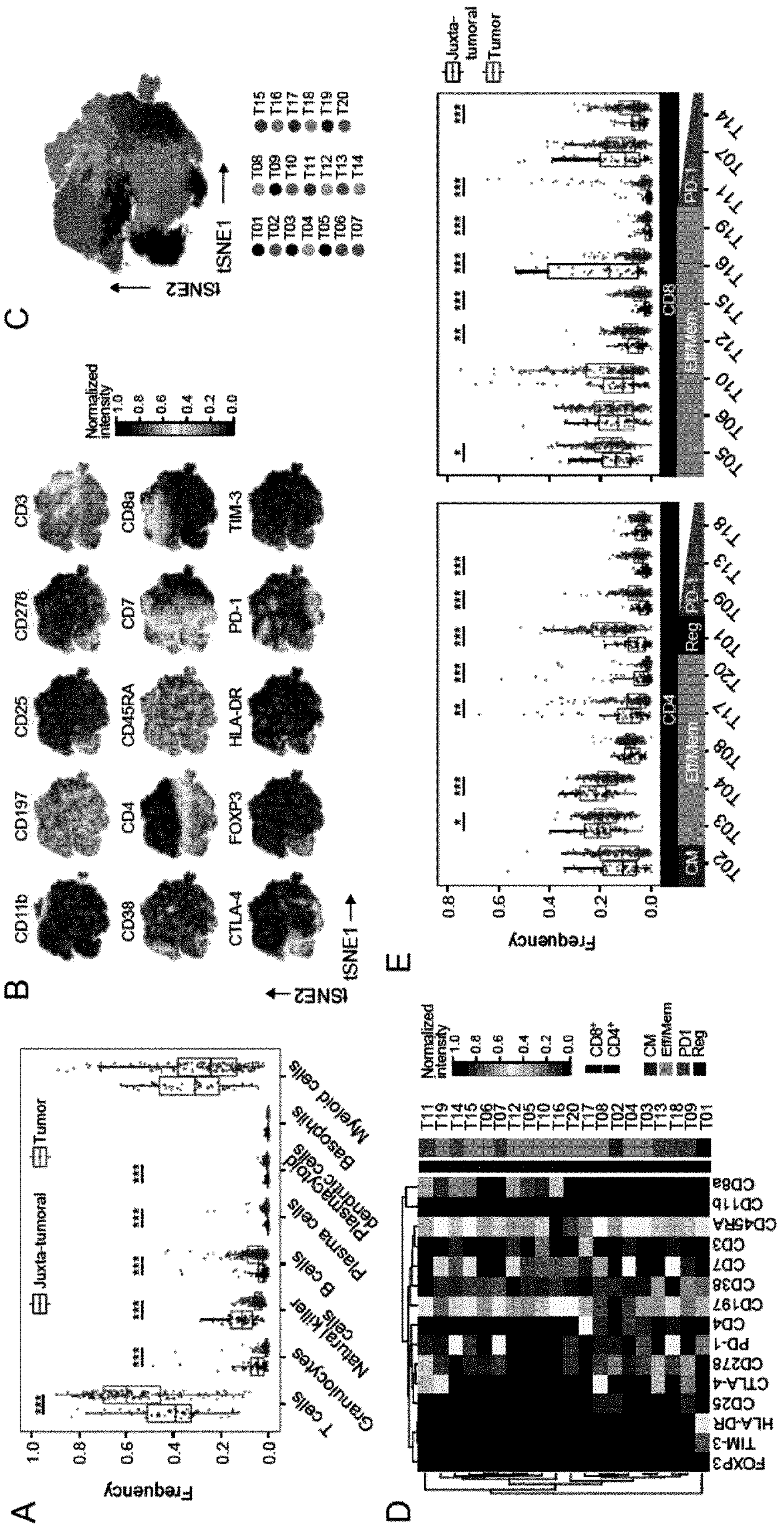
FIG. 2 The breast cancer immune landscape.
Figure 2:
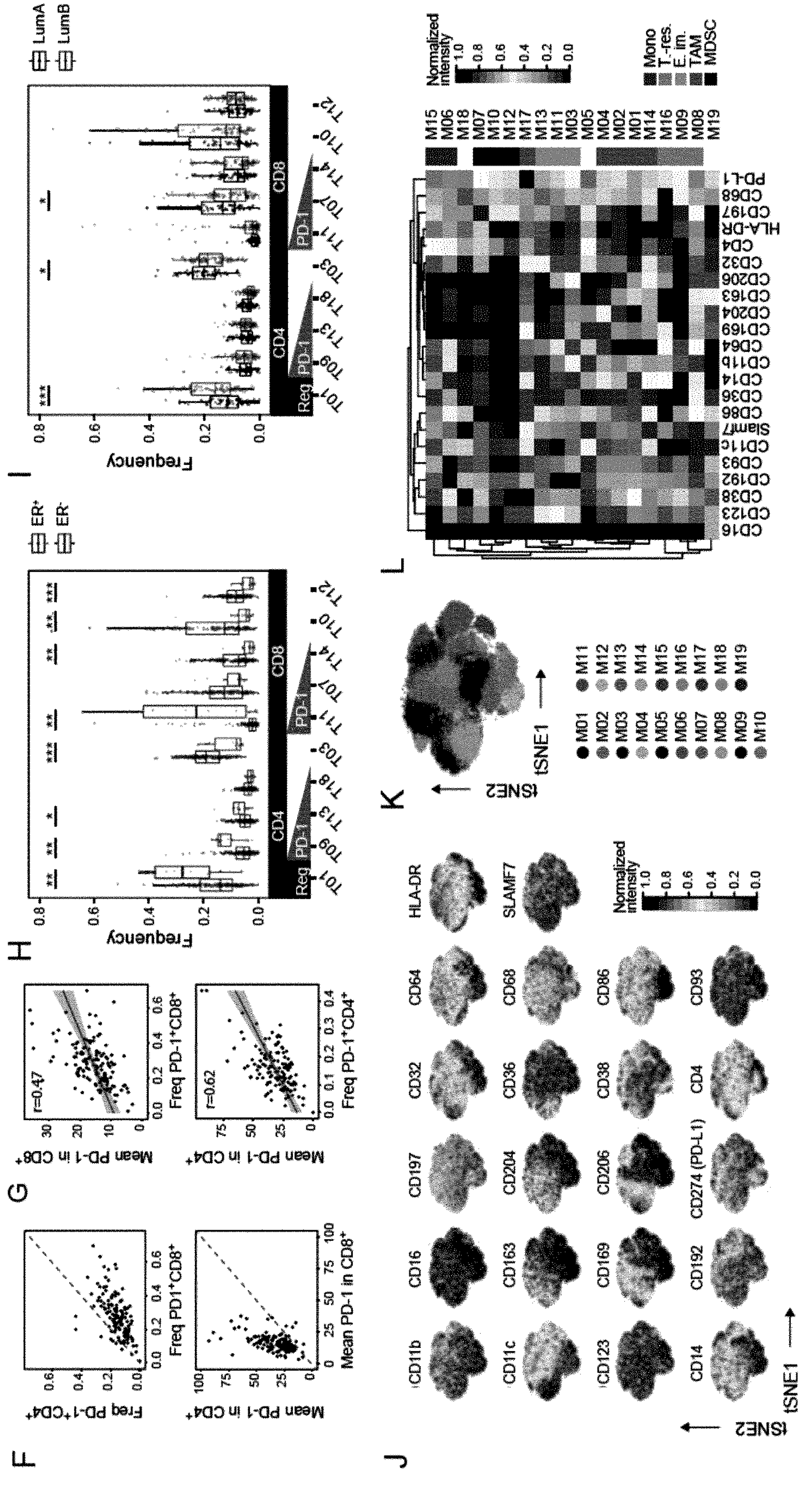
Figure 2:
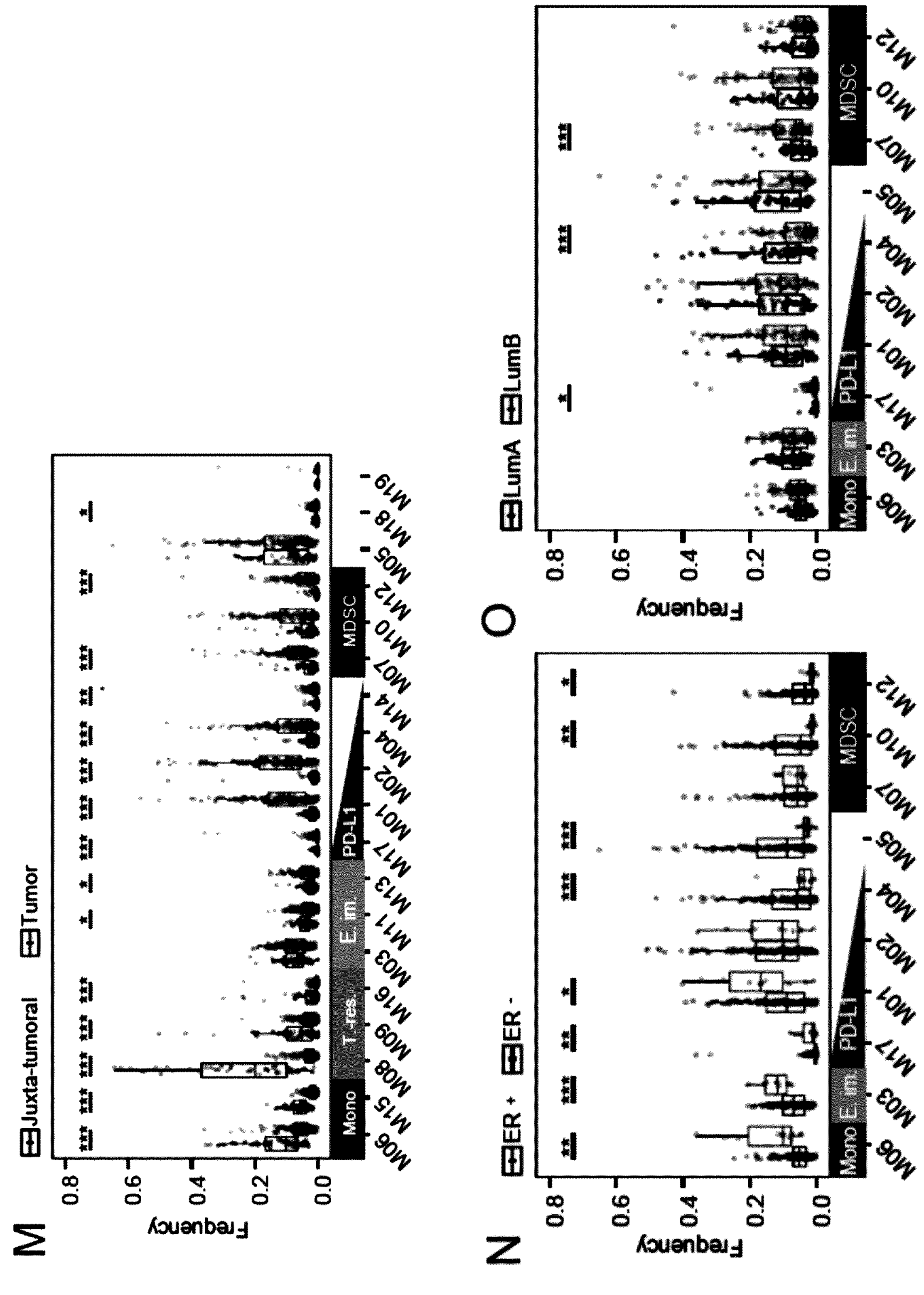
Figure 2:
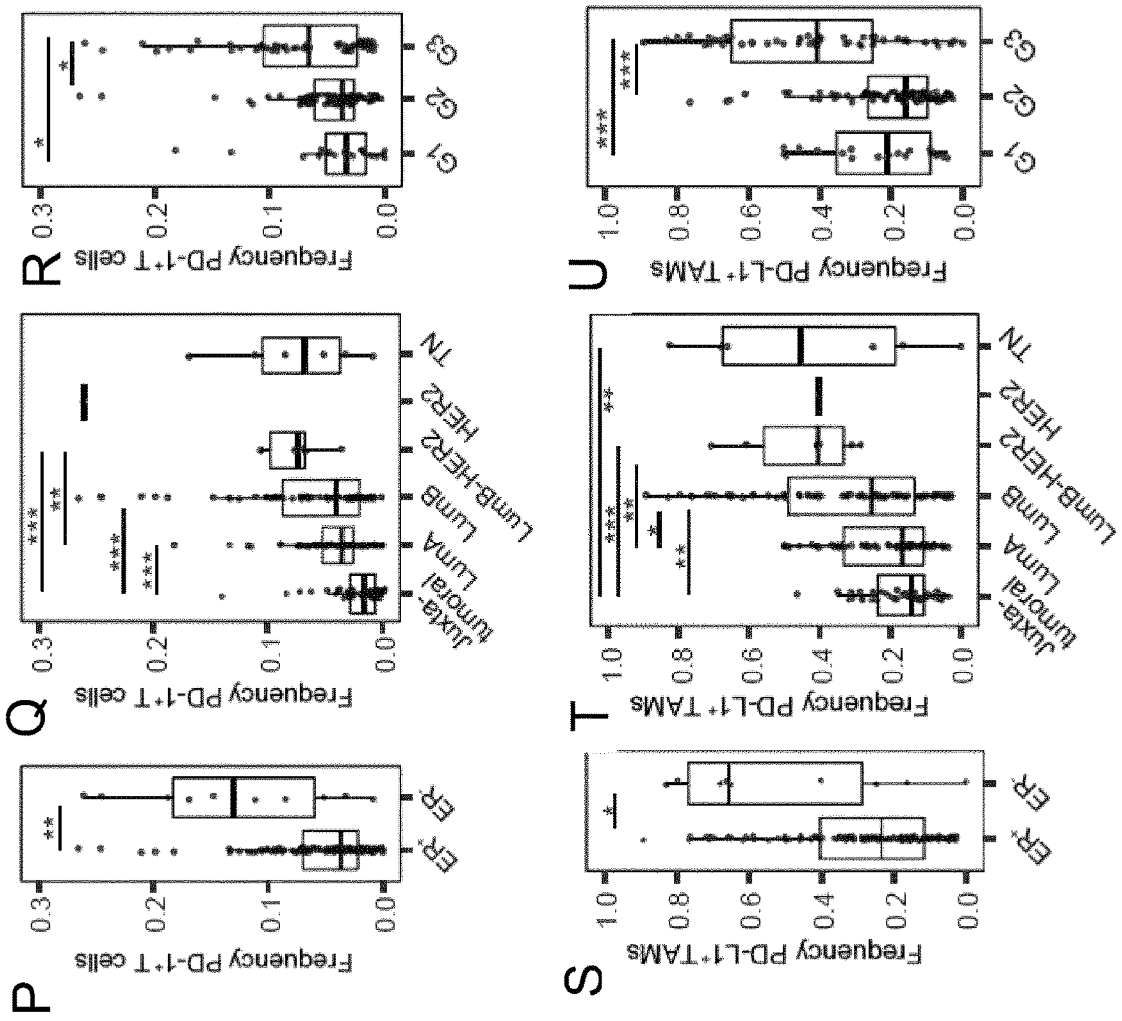

FIG. 2 The breast cancer immune landscape. (A) Frequencies of selected immune cell types in juxta-tumoral and tumor samples. (B) t-SNE plots of the normalized marker expression of 40,000 T cells from all samples. (C) t-SNE of T cells colored by PhenoGraph cluster. (D) Heatmap of normalized T cell marker expression for 20 T cell clusters. CM, central memory; Eff/Mem, effector and memory; Reg, regulatory; PD-1, PD-1. (E) Boxplots showing the frequencies of the $CD4^+$ (left) and $CD8^+$ T cell clusters (right) in juxta-tumoral and tumor samples. (F) $PD\text{-}1^+$ T cell frequency (top) and mean PD-1 expression (bottom) among tumor-derived $CD4^+$ and $CD8^+$ T cells. (G) Comparison of the $PD\text{-}1^+$ T cell frequency and mean PD-1 expression for $CD8^+$ (top) and $CD4^+$ T cells (bottom). (H and I) Frequencies of selected T cell clusters in H) $ER^+$ and $ER^-$ tumors and I) Luminal A and B tumors. (J) t-SNE plots of normalized marker expression of 40,000 myeloid cells from all samples. (K) t-SNE of myeloid cells colored by cluster. (L) Heatmap of normalized myeloid marker expression for 19 myeloid clusters. Mono, monocyte; T.-res, tissue-resident; E. im., early immigrant; TAM, tumor-associated macrophage; MDSC, myeloid derived suppressor cells. (M) Frequencies of the myeloid clusters in juxta-tumoral and tumor samples. (N and O) Frequencies of the indicated myeloid clusters in N) $ER^+$ and $ER^-$ tumors and O) Luminal A and B tumors. Wilcoxon rank-sum test was used for statistical analysis. * $p<0.05$,  $p<0.01$, * $p<0.001$. (P-R) PD-$1^+$ T cell frequencies in P) $ER^+$ and $ER^-$ tumors, Q) juxta-tumoral tissue and tumors by subtype, and R) tumors by grade. (S-U) PD-$L1^+$ TAM frequencies in S) $ER^+$ and $ER^-$ tumors, T) juxta-tumoral tissue and tumors by subtype, and U) tumors by grade.

Figure 3:
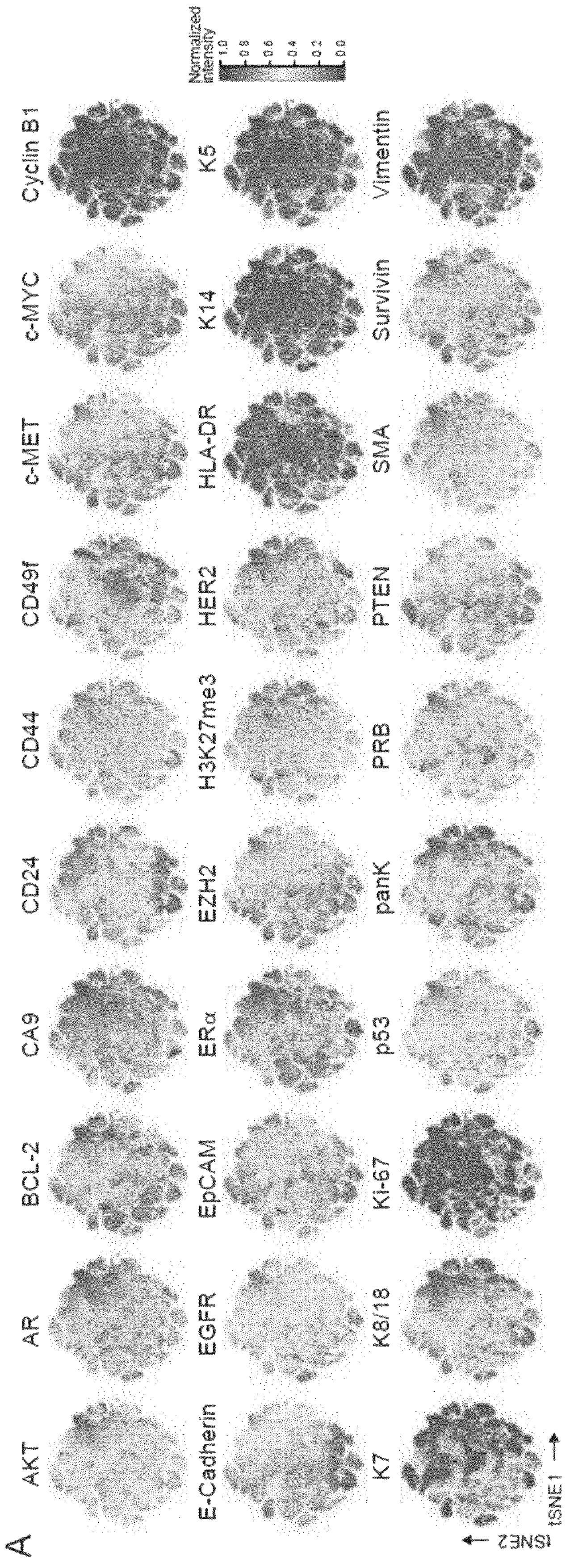
FIG. 3 Tumor cell phenotypic landscape in breast cancer.
Figure 3:
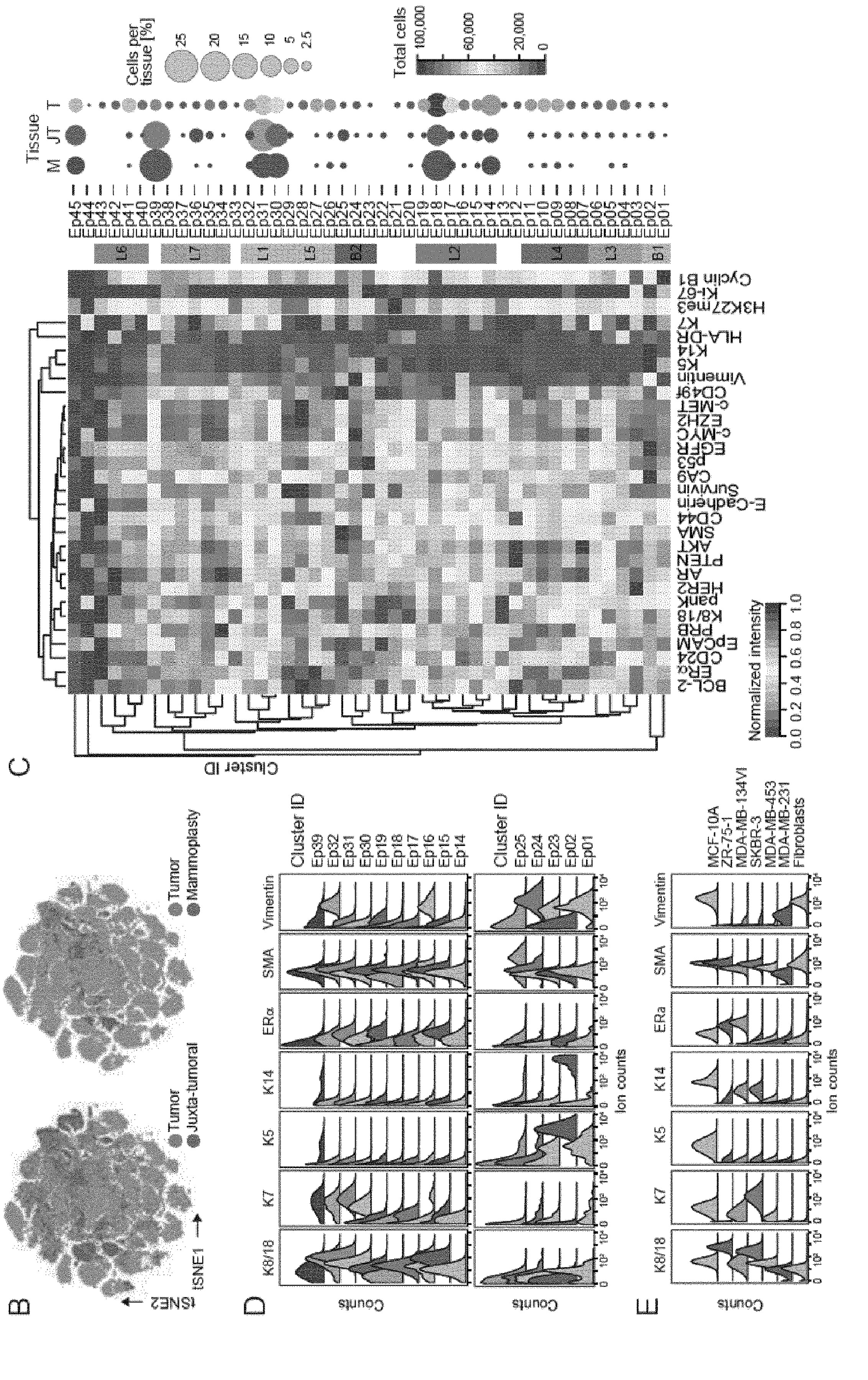
Figure 3:
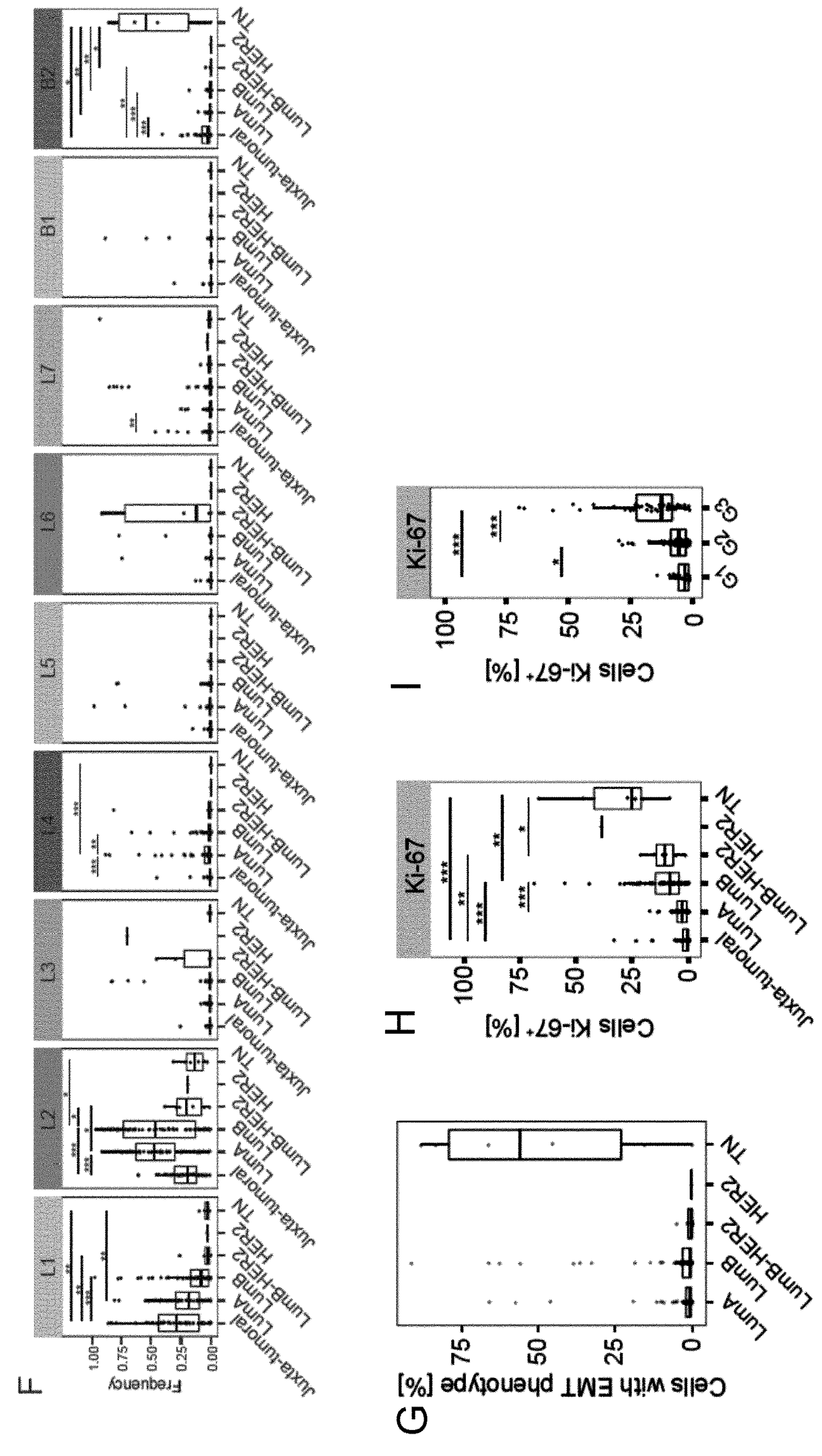

FIG. 3 Tumor cell phenotypic landscape in breast cancer. (A) t-SNE plots of normalized marker expression of 180,000 epithelial cells from all samples. (B) t-SNE highlighting the distribution of cells from tumor, juxta-tumoral, and mammoplasty tissue. (C) Heatmap of normalized tumor cell marker expression for 45 epithelial clusters (left). Percentage and total number of cells from mammoplasty (M), juxta-tumoral (JT), and tumor (T) tissue for each cluster (right). (D and E) Histograms of the expression of epithelial lineage markers in D) cells derived from juxta-tumoral tissue and E) cell lines. (F) Frequencies of cells of individual cluster groups by tumor subtype. Wilcoxon rank-sum test was used for statistical analysis. * $p<0.05$,  $p<0.01$, * $p<0.001$. (G) Percentage of cells with EMT phenotype in tumors by subtype. (H and I) Percentage of Ki-$67^+$ cells in juxta-tumoral and tumor samples by H) subtype and I) grade.

Figure 4:
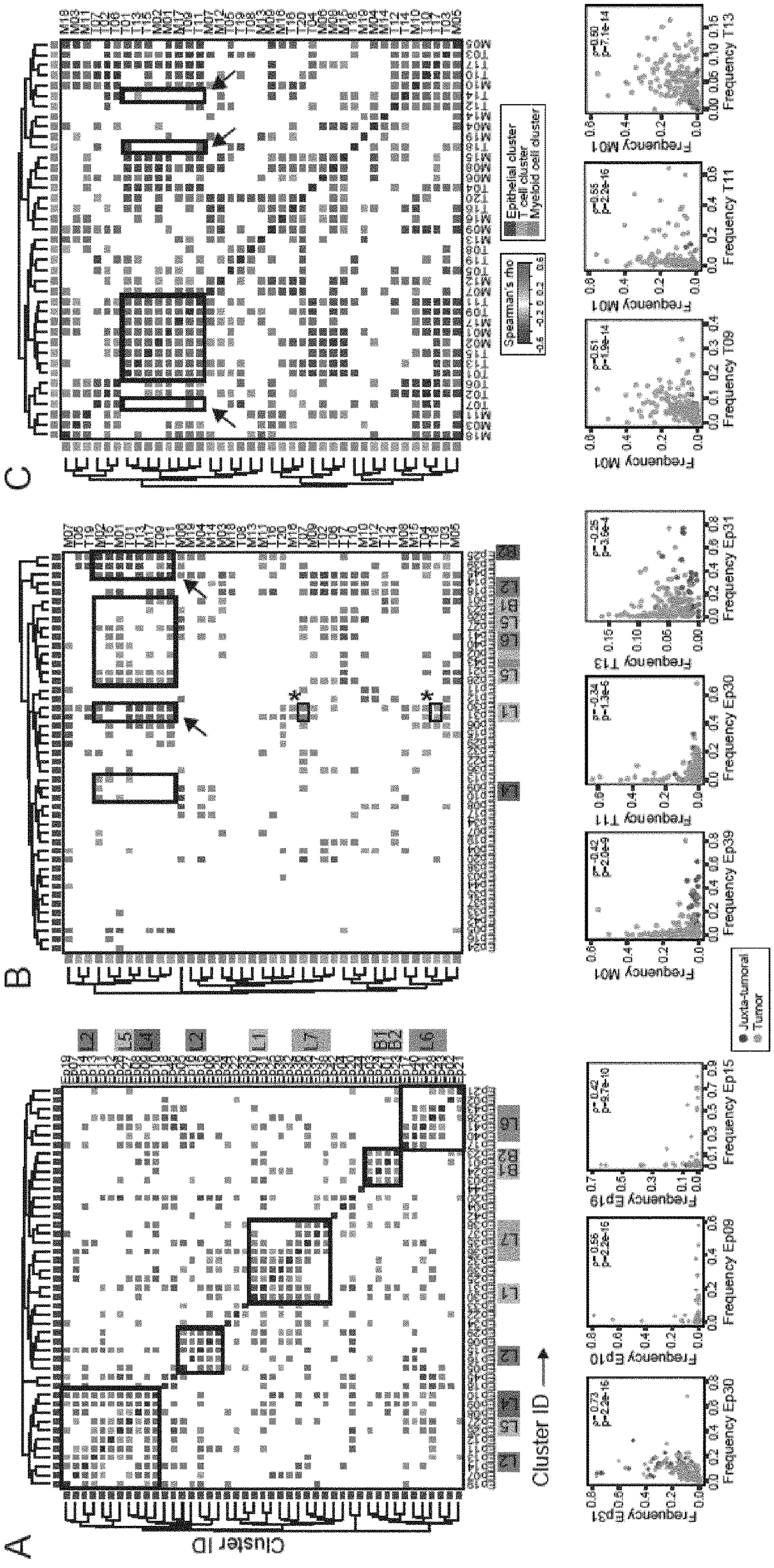
FIG. 4 Breast tumors and their immune environment are interwoven entities.
Figure 4:
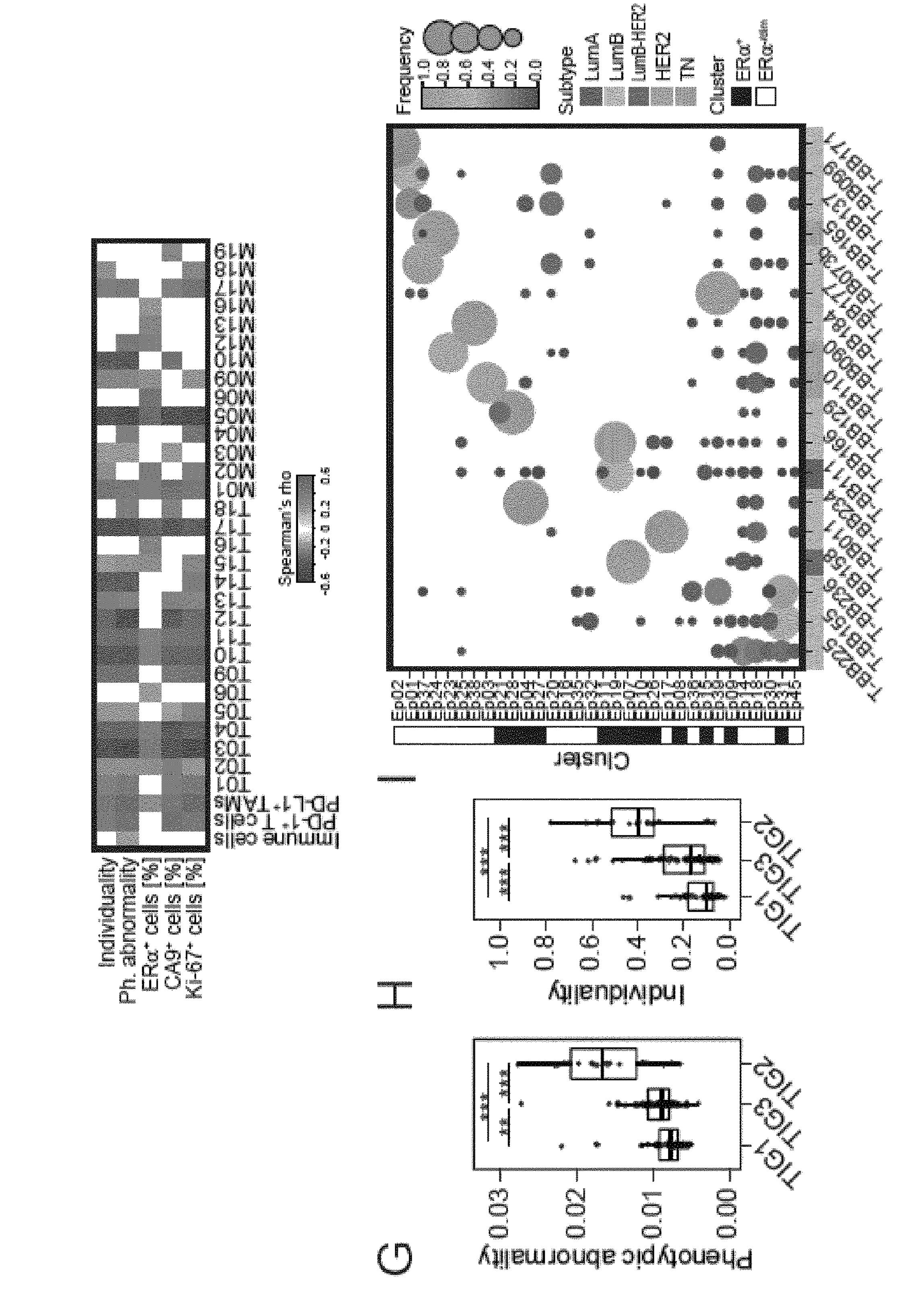
Figure 4:
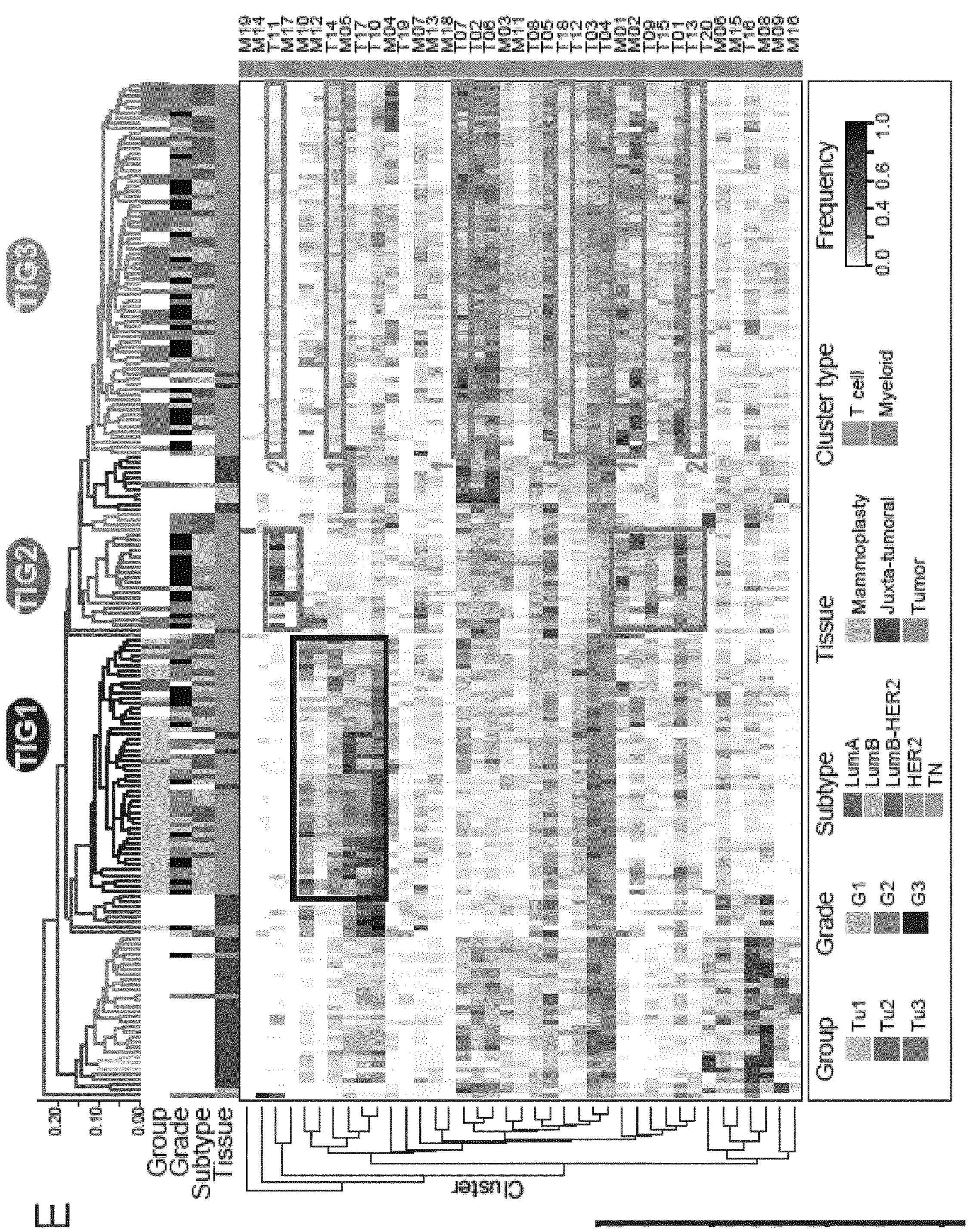
Figure 4:
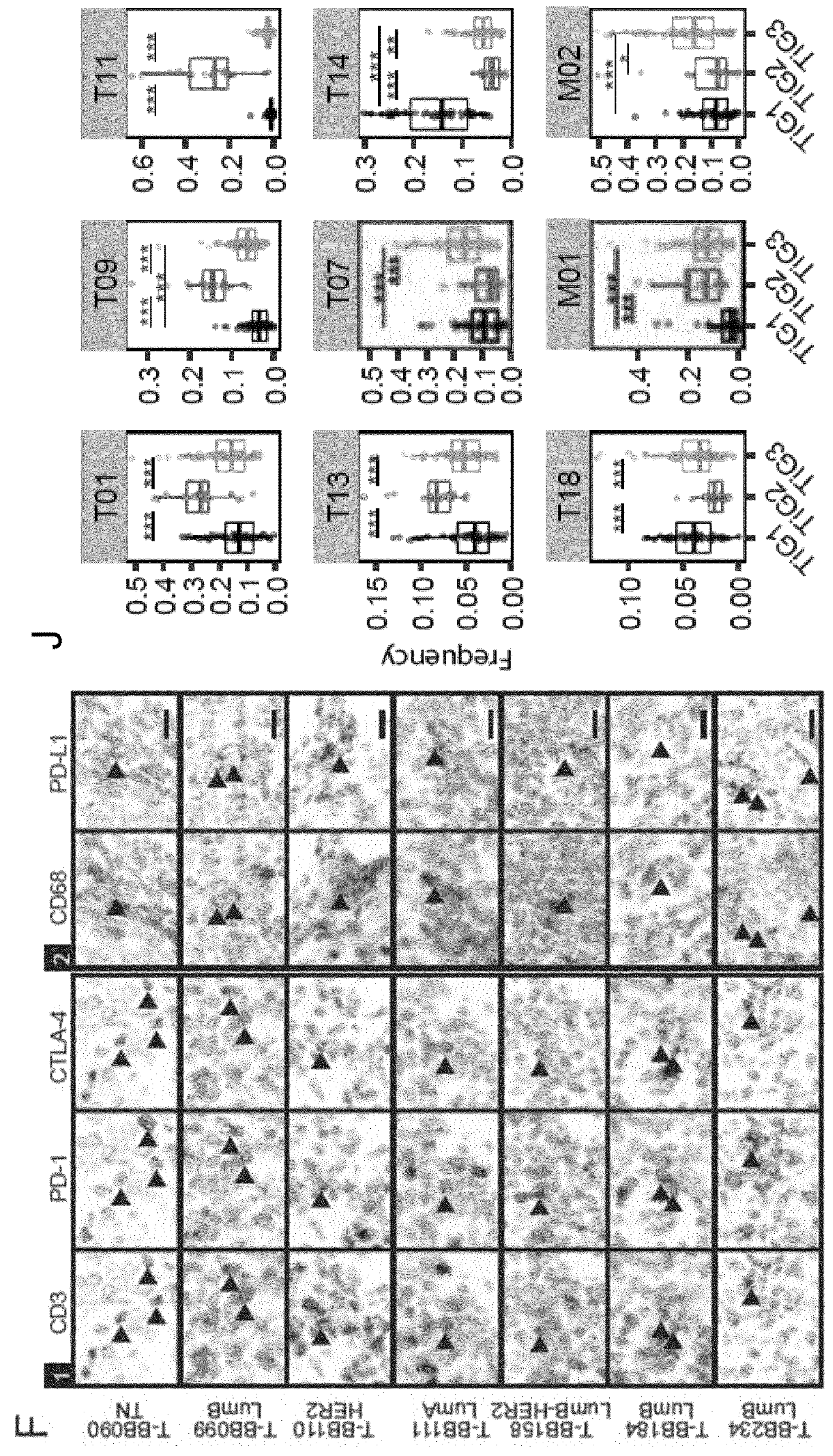
Figure 4:
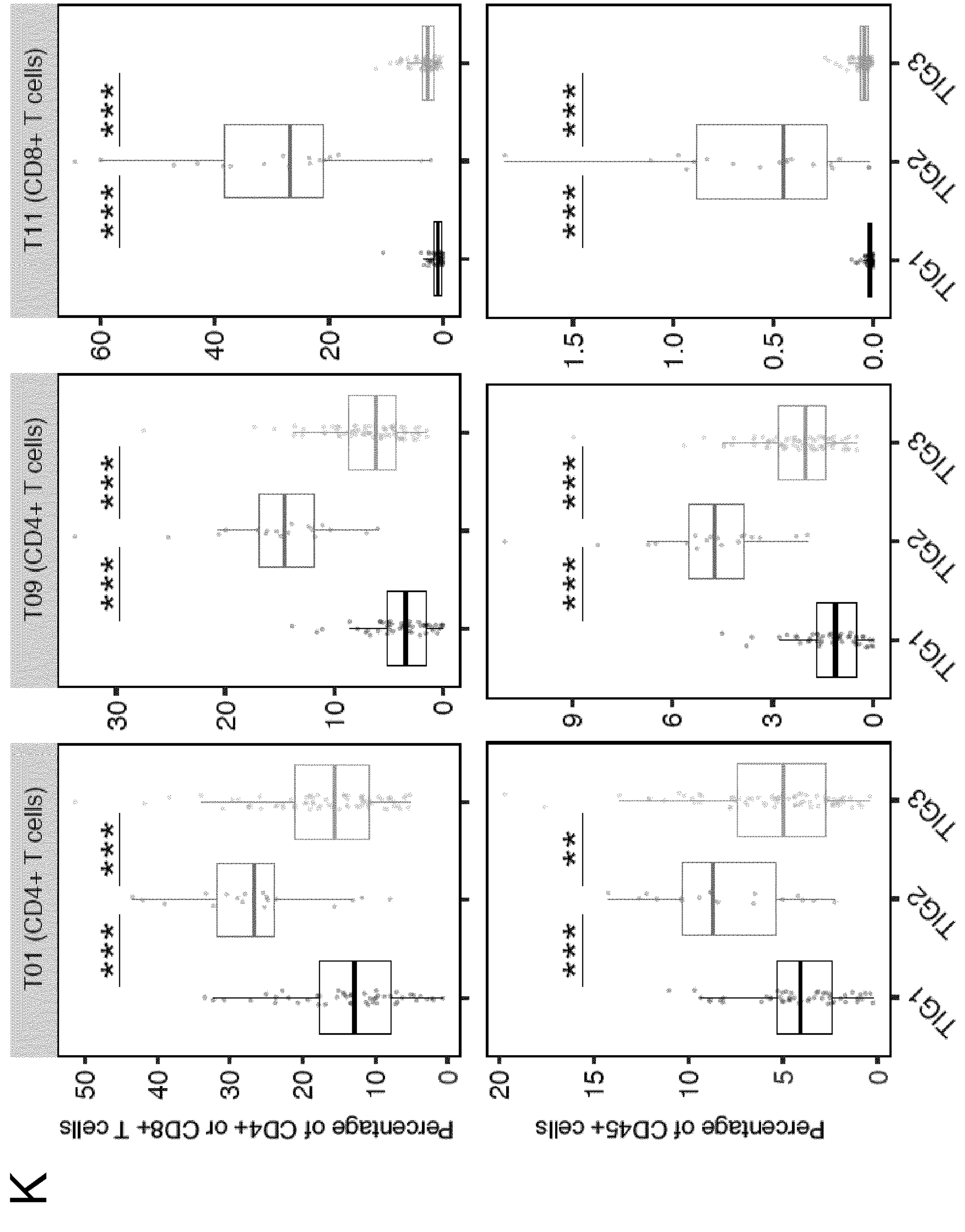

FIG. 4 Breast tumors and their immunoenvironment are interwoven entities. (A-C) Spearman correlation analyses using the frequencies of A) epithelial clusters, B) T cell, myeloid, and epithelial clusters, and C) T cell and myeloid clusters in all samples. Euclidean distance and average linkage were used (upper panels). Frequencies of selected clusters in juxta-tumoral and tumor samples (lower panels). (D) Spearman correlation analysis of T cell and myeloid cluster frequencies with phenotypic abnormality and individuality scores and frequencies of $ER\alpha^+$, $CA9^+$, and Ki-$67^+$ cells in tumors. (E) Heatmap of frequencies of T cell and myeloid clusters in all samples by hierarchical clustering using cosine distance and average linkage. For tumors, the subtype, grade, and three main groups Tu1-3 from FIG. 5A are indicated by color. (F) Pseudo-brightfield images of immunofluorescence staining of indicated tumor samples. Arrowheads indicate PD-$1^+$CTLA-$4^+$ T cells (left) or PD-$L1^+$ TAMs (right). Scale bar, 25 μm. (G and H) Boxplots of G) phenotypic abnormality and H) individuality scores for tumors in tumor immune groups TIG1-3. (1) Cluster frequency map for tumors in TIG2. Tumors and epithelial clusters were sorted by increasing phenotypic abnormality score. A cutoff of $p\leq 0.01$ was used in panels A-D. Wilcoxon rank-sum test was used for panels G and H. * $p<0.05$,  $p<0.01$, * $p<0.001$. (J) Frequency of T cell and TAM phenotypes associated with immunosuppression for TIG1-3. (K) Frequency of T cell phenotypes associated with immunosuppression for TIG1-3 as a function of percentage of CD4+ and CD8+ cells and as a function of CD45+ (i.e. all immune) cells.

EXAMPLES

Example 1: A Single-Cell Proteomic Atlas of Breast Cancer Ecosystems

The inventors performed large-scale mass cytometry profiling of 144 prospectively collected tumors, including 56 Luminal A, 72 Luminal B, six Luminal B-$HER2^+$, one $HER2^+$ and six TN tumors (Table 1) (Coates et al., 2015, Ann. Oncol. 26, 1533-1546). Histopathology divided the samples into 106 invasive ductal, 16 invasive lobular, and 22 mixed/other tumors. An automated system was used to generate single-cell suspensions from all tissue samples (STAR Methods). These samples and seven breast cancer cell lines were mass-tag barcoded (Zunder et al., 2015, Nat. Protoc. 10, 316-333), pooled for antibody staining with 73 antibodies, and simultaneously analyzed by mass cytometry (FIG. 1A). One antibody panel was tumor-cell centric to quantify markers that identify mammary cell types, signaling, proliferation, and survival. The other panel was focused on immune phenotyping and based on the inventors' recent immune cell atlas of clear cell renal cell carcinoma (ccRCC) (Chevrier et al., 2017, Cell 169, 736-749.e18). Application of the inventors' workflow yielded 26 million single-cell profiles with an average of 84.7% live, non-apoptotic cells per sample.

To ensure high data quality, the inventors confirmed the similarity of marker expression of the control samples across barcoding plates and of live cell and immune cell frequencies across antibody panels. Neither sample collection nor processing led to batch effects. Minimal spillover between mass detection channels was corrected using a bead-based compensation workflow (Chevrier et al., 2018, Cell Syst. 6, 612-620.e5). The frequencies of $ER^+$, $PR^+$, $HER2^+$, and Ki-$67^+$ tumor cells determined by mass cytometry were comparable to the matched pathological immunohistochemistry scores.

To visualize the diversity of tumor and non-tumor cells, the inventors generated two-dimensional graphs using the dimensionality reduction algorithm t-distributed stochastic neighbor embedding (t-SNE; Van Der Maaten and Hinton, 2008, J. Mach. Learn. Res. 9, 2579-2605) (FIG. 1B). Most cells were epithelial (expressing EpCAM, E-Cadherin, and epithelial cytokeratins) or immune ($CD45^+$). Endothelial cells ($CD31^+$) and fibroblasts ($FAP^{+/-}$ $SMA^{+/-}$) were less abundant (FIG. 1B). Additional fibroblast subsets and adipocytes were likely among the cells described as "other" (FIG. 1C). To compare cell-type frequencies between tumor and non-tumor tissue, the inventors applied the PhenoGraph algorithm (Levine et al., 2015, Cell 162, 184-197), which partitioned their high-dimensional single-cell data into 42 clusters. Marker expression profiles reliably assigned clusters to cell types (FIGS. 1C and F). Breast tumors were enriched for epithelial cells and contained fewer endothelial cells and fibroblasts than non-tumor tissues (FIG. 1D). Fibroblasts were more abundant in tumors than in juxta-tumoral tissue. The cell type frequencies varied among and between tumor subtypes with a higher frequency of immune cells observed in TN and $HER2^+$samples than in other breast cancer types (FIG. 1E).

Example 2: The Immune Landscape of Breast Cancer

T cells and myeloid cells were the most abundant immune cell types in the inventors' study; fewer natural killer (NK) cells, B cells, granulocytes, plasma cells, and plasmacytoid dendritic cells were detected (FIGS. 2A, S2A-D). Breast tumors were enriched for T cells and B cells and contained a lower frequency of NK cells and granulocytes than juxta-tumoral tissue (FIG. 2A). There was considerable inter-patient variation in tumor-associated immune cell frequencies (FIG. 2A) as previously described.

T cells and macrophages can exert pro-tumor or anti-tumor activities. In-depth analyses of T cells by t-SNE and PhenoGraph identified ten $CD4^+$ and ten $CD8^+$ T cell clusters (T01-T20; FIGS. 2B-D). Most T cell clusters had an effector memory phenotype ($CD197^+$, $CCR7^{low}$, $CD45RA^{low}$), and tumor-associated T cells existed as a phenotypic continuum across the $CD4^+$ and $CD8^+$ lineages (FIG. 2D). Various levels of PD-1 and heterogeneous co-expression of co-inhibitory receptors and activation markers were detected among $CD8^+$ (T11, T14, T07) and $CD4^+$ T cell clusters (T09, T13, T18). An increase in PD-1 expression and in receptor co-expression likely represent increasingly exhausted T cell states. PD-$1^{high}CD8^+$ T cells (T11) expressed the co-inhibitory receptors TIM-3 and CTLA-4 and activation markers HLA-DR and CD38 (FIG. 2D). This phenotype was associated with T cell exhaustion and anti-PD-1 therapy response in melanoma. PD-$1^{high}CD4^+$ T cells (T09, T13) were positive for CTLA-4, CD38, and CD278 but negative for TIM-3 and HLA-DR. PD-$1^{int}CD8^+$(T07, T14) and PD-$1^{int}CD4^+$ T cells (T18) were negative for CTLA-4, TIM-3, HLA-DR, and CD38 (FIG. 2D). T-regs (T01) were identified based on expression of CD4, FOXP3, CD25, and CTLA-4. T-regs and PD-$1^{high}$CTLA-$4^+CD38^+$ T cells (T09, T11, T13) were enriched in tumors compared to juxta-tumoral tissue (FIG. 2E). The majority of patients showed PD-$1^+$ T cells, which comprised up to 26.6% of total tumor-associated T cells, but were rare in juxta-tumoral tissue. Most PD-$1^+$ T cells were found within the $CD8^+$ compartment (FIG. 2F, top panel). However, the mean expression level of PD-1 was higher in $CD4^+$than in $CD8^+$ T cells (FIG. 2F, bottom panel). The mean expression level of PD-1 and the PD-$1^+$ T cell frequency correlated in the $CD4^+$ and $CD8^+$compartments, supporting the hypothesis that these cells result from T cell expansion (FIG. 2G).

$ER^-$ breast cancer subtypes reportedly respond better to immune checkpoint blockade than $ER^+$subtypes. The inventors observed differences in the T cell landscapes of $ER^-$ and $ER^+$tumors including a higher frequency of T-regs in $ER^-$ disease (FIG. 2H). In more than half of $ER^-$ tumors (6/10) but only 12% of $ER^+$tumors (16/132) over 10% of T cells expressed PD-1 (FIG. 2P). Distinct PD-$1^+$phenotypes were separately enriched: PD-$1^{high}$CTLA-$4^+CD38^+$ T cells (T09, T11, T13) were more frequent in $ER^-$ tumors, whereas PD-$1^{int}$CTLA-4-$CD38^-$ T cells (T14) were enriched in $ER^+$tumors (FIG. 2H). Many $ER^+$tumors did, however, show frequencies of PD-$1^{high}$CTLA-$4^+CD38^+$ T cells and T-regs comparable to or higher than $ER^-$ tumors (FIG. 2H). Therefore, the inventors' data support that patients with $ER^-$ tumors are candidates for immunotherapy and indicate that a subset of patients with $ER^+$tumors should benefit, too.

$ER^+$tumors can be divided into Luminal A and Luminal B based on low and high proliferation, respectively. More than 10% of T cells expressed PD-1 in 18% of Luminal B tumors but only 7% of Luminal A tumors (FIG. 2Q). PD-$1^{int}$CTLA-$4^-CD38^-$ T cells (T07) were more frequent in Luminal A disease and T-regs were enriched in Luminal B tumors (FIG. 2I). The inventors also observed distinct T cell landscapes in tumors of different grades. PD-$1^+$ T cells accounted for more than 10% of T cells in 28% of grade 3 tumors, 9% of grade 2 tumors, and 10% of grade 1 tumors (FIG. 2R). Grade 3 tumors had more PD-$1^{high}$CTLA-$4^+CD38^+$ T cells (T09, T11) and fewer PD-$1^{int}$CTLA-$4^-CD38^-$ T cells (T07, T14) than tumors of lower grades.

This demonstrates that an immunosuppressed T cell landscape is linked to poor prognosis tumors, including $ER^-$, high proliferation, and high-grade tumors, but is also observed in a subset of $ER^+$ tumors.

Example 3: Breast Tumors are Enriched for Immunosuppressive Macrophage Phenotypes To characterize TAM populations, t-SNE and PhenoGraph were applied to all myeloid cells (FIG. 2J), resulting in 19 myeloid clusters (M01-M19) of five categories: i) CD14-expressing classic (M06, $CD14^+CD16^-$) and inflammatory monocytes (M15, $CD14^{int}CD16^+$), ii) early immigrant macrophages (M03, M11, M13, HLA-$DR^{int}CD192^+$), iii) tissue-resident macrophages (M08, M09, M16, $CD206^+$ HLA-$DR^{int}$), iv) TAMs (M01, M02, M04, M14, M17, $CD64^{high}$HLA-$DR^{high}$), and v) myeloid-derived suppressor cells (MDSCs; M07, M10, M12, HLA-DR-$CD38^+$) (FIGS. 2K-L). Consistent with previous reports, the myeloid phenotypic space differed between tumor and juxta-tumoral regions (FIG. 2M). In 80% of tumors at least 10% of myeloid cells were PD-$L1^+$. The PD-$L1^+$ TAMs were phenotypically heterogeneous: TAMs in cluster M01 expressed pro-tumor markers CD204, CD206, CD163, and CD38 and anti-tumor marker CD169, whereas TAMs in M02 expressed CD204, CD169, and intermediate levels of CD163 and CD38, and TAMs in M17 expressed CD169 and CD38 (FIG. 2L). Expression of CD38 is associated with immunosuppressive macrophages in ccRCC patients and with MDSC-mediated T cell suppression in colorectal cancer. The inventors' results therefore link CD38 and PD-L1 and confirm co-expression of pro- and anti-inflammatory markers by tumor-associated myeloid cells. Tumors were depleted of tissue-resident macrophages (M08, M09), classical circulating (M06), and pro-inflammatory (M15) monocytes compared to juxta-tumoral tissue (FIG. 2M).

Infiltration by TAMs is associated with aggressive disease. $ER^-$ tumors contained higher frequencies of M01 and M17 PD-$L1^+$ TAMs and fewer myeloid cells with M04, M05, M10, or M12 phenotypes compared to $ER^+$tumors (FIG. 2N). A subset of $ER^+$tumors had M01 and M02 PD-$L1^+$ TAMs at frequencies comparable to or higher than $ER^-$ tumors (FIGS. 2N and 2S). Luminal B tumors contained more myeloid cells with M07 or M17 phenotype, less with M04 phenotype, and more PD-$L1^+$ TAMs compared to Luminal A tumors (FIGS. 20 and 2T). PD-$L1^+$ TAMs were enriched in grade 3 tumors compared to grade 2 tumors (FIG. 2T). Grade 3 tumors contained fewer cells with M04 or M05 phenotype but more classical monocytes (M06) than lower grade tumors.

Example 4: Tumor Epithelial Cells are Heterogeneous and Phenotypically Abnormal

The analysis of epithelial cells from tumor and non-tumor tissues (STAR Methods) revealed bimodal and gradient-like expression of epithelial markers, indicative of many distinct cell phenotypes (FIGS. 3A-B). A consensus clustering approach implemented in PhenoGraph revealed 45 epithelial clusters (Ep01-Ep45). Hierarchical clustering classified these into seven luminal groups L1-L7 and two basal groups B1 and B2 based on marker expression (FIG. 3C).

The inventors identified luminal and myoepithelial cells in mammoplasty and juxta-tumoral tissue based on lineage marker expression patterns (FIGS. 3C-D). Mammary epithelial cell lines confirmed the reliability of these patterns (FIG. 3E). About 63% of cells from mammoplasties and 77% of juxta-tumoral tissue-derived cells were members of groups L1 and L2, characterized by expression of K7/8/18 and low levels or no ERα (FIGS. 3C-D). Strong expression of EpCAM and low levels of adhesion integrin CD49f indicated luminal cell maturity (FIG. 3C). Proliferating (Ki-67*) non-tumor luminal cells were also identified. About 55% of tumor-derived cells were members of groups L1 and L2, showing that differentiated normal-like luminal cells were abundant in tumor samples.

Groups L3-L7 were dominated by tumor cells (FIG. 3C). Group L3 phenotypes showed high levels of EpCAM and CD49f and low ERα expression (FIG. 3C), characteristics of luminal progenitor cells. Group L4 phenotypes displayed high levels of hormone receptors ERα, PRB, and AR and receptor tyrosine kinases HER2, EGFR, and c-MET (FIG. 3C), which are involved in tumor cell proliferation and migration. Co-expression of these receptors with ERα or HER2 can confer resistance to anti-ERα and anti-HER2 treatments. Strong receptor tyrosine kinase expression and high levels of the methyltransferase EZH2, its target H3K27me3, and anti-apoptotic factors Survivin and BCL-2 were observed in group L5 (FIG. 3C). EZH2-induced epigenetic alterations can equip tumor cells for expansion and invasion. Survivin and BCL-2 are associated with cell death evasion and risk of recurrence in $ER^+$ disease. Group L6 phenotypes expressed K7/8/18, ERα, HER2, low levels of CD49f, and high levels of E-Cadherin and CD24 (FIG. 3C), indicative of luminal cell maturity with ERα and HER2 pathway activity. Group L7 phenotypes were $ER\alpha^-$ and $HER2^-$, and expressed $HLA\text{-}DR^+$, a surface receptor associated with tumor immunogenicity (FIG. 3C). Lack of ERα and HER2 is associated with resistance to anti-ERα and anti-HER2 treatments. $Ki\text{-}67^+$ luminal tumor cells were found in all luminal cluster groups and were most frequent in group L7.

Group L1-L7 phenotypes were differently distributed across tumor subtypes. Group L1 and L2 phenotypes indicative of mature luminal cells and group L4 and L5 phenotypes strongly expressing ERα were more frequent in Luminal A and B tumors than in $HER2^+$ and TN tumors (FIG. 3F). Proliferating group L7 phenotypes were frequent in several Luminal B, a few Luminal A, and one TN tumor. Luminal B-$HER2^+$ and $HER2^+$ tumors contained cells from groups L3 and L6 (FIG. 3F). Many luminal tumors contained fewer $K7^+$ and more $K8/18^+$ cells than adjacent non-tumor tissue, suggesting a cytokeratin switch possibly induced by upregulated PI3K/AKT signaling. $ER\alpha^+$ cells varied between 2%-91% (median 26.7%, IQR 26.8%) and $ER\alpha^+AR^+$ cells varied between 0%-44% (median 1.7%, IQR 4.3%) in $ER^+$ tumors.

The inventors identified basal cell phenotypes in group B1 based on expression of K5/14 and Vimentin and in group B2 based on expression of SMA, Vimentin, and low levels of K5/14.

All basal phenotypes lacked expression of K7/8/18, ERα, and HER2 (FIG. 3C). Non-tumor cells with basal phenotype were likely myoepithelial cells (FIG. 3E). In contrast to juxta-tumoral tissue, myoepithelial cells were sparse in mammoplasty samples, possibly a consequence of obesity. Basal-like tumor cells displayed high levels of Ki-67, EGFR, and tumor suppressor p53. Overexpression of EGFR and p53 and lack of ERα and HER2 are characteristics of aggressive, difficult to treat cancers. Both basal-like and luminal ERα HER2-$PRB^{dim}$ phenotypes expressed high levels of Survivin, indicative of survival pathway activity. The majority of luminal tumors (126/130) did not contain cells with basal phenotype, consistent with the absence of myoepithelial cells. Cells of group B2 were abundant in TN tumors (FIG. 3F) in line with a basal-like molecular subtype. Tumor cells with basal phenotype and tumor cells in luminal clusters Ep16 and Ep32 co-expressed EpCAM, E-Cadherin, and Vimentin, an epithelial-mesenchymal transition (EMT) phenotype associated with tumor cell invasion and resistance to chemotherapy. Tumor cells with EMT phenotype were found in TN tumors and in several Luminal A and B tumors (FIG. 3G). All subtypes except Luminal A had elevated frequencies of proliferating cells compared to juxta-tumoral tissue (FIG. 3H). Proliferation was strongest in grade 3 tumors (FIG. 3I).

Example 7: A Breast Tumor and its Immunoenvironment are Interwoven Entities and Both are Important for Classification Networks of tumor cell and tumor-host cell interactions drive disease progression and are promising targets for drug intervention. To systematically elucidate homotypic and heterotypic tumor and immune cell relationships, the inventors performed pairwise Spearman correlation analyses of the frequencies of all cell phenotype clusters in all samples (FIGS. 4A-C). Homotypic epithelial cell relationships were found between phenotypes from different cluster groups (FIG. 4A, black rectangles). Non-tumor luminal phenotypes such as Ep30 and Ep31 (group L1) were correlated, whereas tumor-specific phenotypes, such as Ep09 and Ep10 (group L4) or Ep19 and Ep15 (group L2), were often separately enriched, reflecting phenotype dominance and tumor individuality (FIG. 4A). Immunosuppressive phenotypes T-regs (T01), $PD\text{-}1^{high}CTLA\text{-}4^+CD38^+$exhausted T cells (T09, T11, T13), and $PD\text{-}L1^+$ TAMs (M01, M02, M17) correlated with tumor cell phenotypes from L4, L5, L6, and B1 (FIG. 4B, rectangles without arrows). The frequencies of non-tumor phenotypes in groups L1 and L2 and cluster Ep39 were inversely linked to these immunosuppressive phenotypes (FIG. 4B, rectangles marked with arrows) but correlated with $PD\text{-}1^{int}CTLA\text{-}4^-CD38^-$ phenotypes T07 and T18 (FIG. 4B, rectangles marked with asterisks). Relationship analysis among tumor-associated immune cells revealed that T-regs and $PD\text{-}L1^+$ TAM phenotypes correlated with $PD\text{-}1^{high}CTLA\text{-}4^+CD38^+$exhausted T cell phenotypes, suggesting immunosuppressive interactions (FIG. 4C, square and biaxial plots). T-regs and $PD\text{-}L1^+$ TAMs did not or only inversely correlate with $PD\text{-}1^{int}CTLA\text{-}4^-CD38^-$ T cell phenotypes (FIG. 4C, rectangles marked by arrows). Furthermore, immunosuppressive patterns correlated with tumor phenotypic abnormality and individuality scores, with hypoxia, and proliferation (FIG. 4D).

The inventors also observed a correlation between immunosuppressive TAMs and T cells and the abundance of $ER\alpha^+$ cells (FIG. 4D), demonstrating that estrogen signaling is a shaping force in the tumor ecosystem. The epithelial-immune relationships in tumors differed from those of matched juxta-tumoral tissues; higher numbers of homotypic epithelial and T cell and heterotypic T cell-TAM relationships were detected in tumors.

In the inventors' ecosystem-based classification 24% of tumors were singletons. Since the relationship analyses indicated considerable structure within the tumor immunoenvironment, the inventors hypothesized that singleton tumors might be grouped based on immunoenvironmental similarities to guide patient selection for immune-targeted therapies. Repeating the hierarchical clustering using only the immune cluster frequencies resulted in three tumor immune groups (TIG1-3) heterogeneous for tumor subtypes. Juxta-tumoral and mammoplasty tissues grouped together (FIG. 4E). Of the previous singleton tumors, 6% were placed into TIG1, 32% in TIG2, and 50% into TIG3. Tumors in TIG1 were enriched for clusters M05, M10, M12, T10, T14, and T17 (FIG. 4E, black rectangle). TIG3 tumors displayed high frequencies of PD-L1$^+$ TAMs (M01, M02, M17) and PD-1$^{int}$CTLA-4$^-$CD38$^-$ T cells (T14) (FIG. 4E, blue rectangles #1) but low levels of PD-1$^{high}$CTLA-4$^+$CD38$^+$exhausted T cells (T09, T11, T13) (FIG. 4E, blue rectangles #2). In contrast, tumors in TIG2 exhibited high frequencies of T-regs (T01), PD-L1$^+$ TAMs, and PD-1$^{high}$CTLA-4$^+$CD38$^+$exhausted T cells (FIG. 4E, red rectangles). Therefore, the tumor immune groups presented distinct relationships among T-regs, PD-1$^+$ T cells, and PD-L1$^+$ TAM phenotypes (FIG. 4J, K). Juxta-tumoral samples found in TIG1 and TIG3 displayed high frequencies of PD-1$^{int}$CTLA-4$^-$CD38$^-$ T cells or PD-L1$^+$ TAMs unlike other non-tumor samples (FIG. 4E). In four of the five patients with juxta-tumoral tissue in TIG1 or TIG3, lymph nodes near the tumor had been invaded, suggesting that these phenotypes resulted from a tumor-associated immune response.

Tumors of different subtypes, including ER$^+$ and ER$^-$ tumors, grouped in TIG2, raising the question whether those immune cells abundant in TIG2 were localized proximally in the tumor ecosystem. The inventors assessed the spatial distribution of PD-L1$^+$ TAMs and PD-1$^+$ and PD1$^+$CTLA-4$^+$ T cells in tissue sections of TIG2 tumors by immunofluorescence imaging and found these cells both in the tumor stroma and within tumor epithelium in ER$^+$ and ER$^-$ disease (FIG. 4F). The TIG2 tumors had higher phenotypic abnormality scores than TIG1 and TIG3 tumors (FIG. 4G), suggesting that tumor phenotypic deviation from non-tumor tissue is associated with changes in the tumor immune landscape. TIG2 tumors also had higher individuality scores than TIG1 and TIG3 tumors and revealed unique tumor cell phenotype compositions (FIGS. 4H-I). All TIG2 tumors contained ERα$^-$ cells, ranging from 98% to 15% of the tumor cell population. Among ERα$^-$ cells, the inventors found EMT phenotypes (Ep01, Ep02, Ep16, Ep23-25, Ep32) in 61% of TIG2 tumors and HLA-DR$^+$ phenotypes (Ep01, Ep37, Ep38) in 39% of TIG2 tumors (FIG. 41). ERα$^+$ phenotypes were mainly from groups L4 (Ep07-11) and L5 (Ep26-29) and co-expressed PRB, HER2, and AR with high levels of pro-survival BCL-2 and Survivin. Thus, in addition to an immunosuppressive environment, TIG2 tumor ecosystems contained multiple tumor cell populations with potential to escape common cancer therapies.

Discussion

Communication between heterogeneous tumor cells, infiltrating T cells, and macrophages shapes the breast cancer ecosystem with impact on disease progression and clinical outcome. The inventors constructed an extensive single-cell atlas of human breast cancer ecosystems by large-scale mass cytometry profiling of 26 million cells from 144 tumors, 46 juxta-tumoral samples, and tissue from four reduction mammoplasties. This atlas reveals vast phenotypic diversity of mammary epithelial and immune cells, phenotypic abnormalities of tumor cells, and tumor individuality and highlights tumor-immune cell relationships enabling an ecosystem-based patient classification.

Most cases in the inventors' study were luminal ER$^+$ breast cancers. Despite generally favorable prognosis, about 30% of patients with ER$^+$ disease develop therapy resistance and metastases. The inventors found that tumor-derived epithelial cells were phenotypically much more diverse than cells from non-tumor tissue. Tumors of all clinical subtypes displayed striking individuality in cellular phenotypic composition. These findings might underlie the differential treatment responses and relapse rates among ER$^+$ breast cancer patients. Although multiple tumor cell phenotypes co-existed in all tumor ecosystems, frequently one phenotype was dominant, possibly reflecting the expansion of the fittest tumor subclone as suggested by genomics. Phenotype dominance can be particularly important for disease progression if associated with resistance, such as the dominant ERα$^-$ HER2$^-$ Survivin$^{high}$ phenotypes the inventors found in tumors resistant to neoadjuvant chemotherapy. Phenotypic abnormality scores were higher for tumor cells of Luminal B, Luminal B-HER2$^+$, TN, and grade 3 tumors than of Luminal A and lower grades. Given that HER2$^+$ and TN tumors were underrepresented in our cohort, the inventors expect that expanded analyses of these subtypes will also reveal tumor cell heterogeneity and tumor individuality as apparent in ER$^+$ tumors.

Single-cell RNA sequencing of a few tumors suggested that tumor-associated T cells and myeloid cells are phenotypically diverse, which is supported by our analysis of a large cohort. The inventors found that PD-1$^+$ T cells and PD-L1$^+$ TAMs were common in all breast cancer subtypes. Receptors relevant to T cell exhaustion (PD-1, CTLA-4, TIM-3) and activation (HLA-DR, CD38) as well as pro-tumor (CD204, CD206, CD163) and anti-tumor TAM markers (CD38, CD169) were heterogeneously expressed, reminiscent of findings in breast cancer and ccRCC. Recent work indicated that PD-1$^+$ T cells follow a gradient of dysfunction ranging from low to high exhaustion. The inventors' data confirmed a continuum of T cell exhaustion states linked to increasing PD-1 levels. The inventors found different combinations of immune checkpoint molecules associated with high PD-1 expression in both CD4$^+$ and CD8$^+$ T cell populations and identified CD38 as a marker of T cell exhaustion in breast cancer. Immunosuppressive T cell and TAM phenotypes correlated with tumor-specific luminal ERα$^+$ and ERα$^-$ phenotypes that expressed specific receptor tyrosine kinases and pro-survival proteins. Since interactions between tumor cells, T cells, and TAMs are promising targets for therapy, follow-up experiments should elucidate the functional roles of distinct tumor and immune cell populations in breast cancer ecosystems.

The inventors' data revealed that the frequency of ERα$^+$ cells in ER$^+$ tumors was linked to tumor individuality. In Luminal B tumors, the frequency of ERα$^+$ cells correlated with PD-L1$^+$ TAMs and exhausted T cell phenotypes, supporting the notion that hormone receptor signaling shapes the tumor ecosystem. The success of immune checkpoint therapy in ER$^+$ breast cancer patients has been limited. Here, the inventors showed that 18% of Luminal B tumors exhibited patterns of strong T cell exhaustion akin to ER$^-$ tumors, suggesting that some ER$^+$ patients could benefit from neoadjuvant or early adjuvant anti-PD-1/PD-L1 therapy targeting the primary tumor. The inventors' study identified patterns within the tumor and immune ecosystem that are tumor-stratifying independent of subtype and grade. Therefore, assessing the entire cancer ecosystem should be considered for the design of precision therapies targeting the tumor and its immunoenvironment and for patient selection for immunotherapy clinical trials. Further studies are needed to confirm this suggestion.

The inventors' mass cytometry approach has limitations. First, antibody choices might bias phenotyping. Antibodies in the inventors' tumor panel were selected based on studies delineating mammary epithelial cell states, gene expression, and protein signatures enriched in breast cancer subtypes. The immune antibody selections were based on the inventors' recent ccRCC immune atlas (Chevrier et al., 2017, Cell 169, 736-749.e18). All antibodies were thoroughly validated. Second, tissue dissociation into single-cell suspensions potentially alters cell-surface molecules. The recapitulation of known cell phenotypes using the inventors' panels indicates small effects. Third, data-driven clustering is sensitive to the choice of clustering parameters. PhenoGraph is a reproducible single-cell clustering method (Weber and Robinson, 2016, Cytom. Part A 89, 1084-1096) and yielded epithelial and immune clusters that recapitulated known mammary epithelial, T cell, and TAM phenotypes. Spatial context and functional roles of these phenotypes must be addressed in additional experiments. Fourth, although our tumor samples were of about 0.125 $cm^3$ volume, which is much larger than volumes typically analyzed in pathology studies, tumor regions might differ. Fifth, our ecosystem-based patient grouping is a function of the measured markers and the patient cohort. Since the inventors' samples were collected prospectively, relationship analysis to clinical outcome or treatment response was not possible.

New treatment approaches are needed to increase the success of breast cancer precision medicine. A first step is to comprehensively describe the complex cellular and phenotypic diversity of tumor ecosystems and the relationships among its components for a large number of patients. Here the inventors provide such an atlas of breast cancer ecosystems. This atlas will be a valuable resource for future research to identify clinically relevant cell phenotypes and relationships in the tumor ecosystem for patient stratification and precision medicine applications.

Materials and Methods

Clinical Samples

Primary mammary gland tissue and health-related data were collected after obtaining written informed consent from patients at the University Hospital Basel (Switzerland), the University Hospital Zurich (Switzerland), and in collaboration with the Patient's Tumor Bank of Hope (PATH, Germany) at the breast cancer centers at St. Johannes Hospital Dortmund and Institute of Pathology at Josefshaus (Germany) and the University Hospital Giessen and Marburg, Marburg site (Germany). Tissue and health-related data were collected under approval of the Ethics Committee Northwest/Central Switzerland (#2016-00067), the Ethics Committee Zurich (#2016-00215), and the faculty of medicine ethics committee at Friedrich-Wilhelms-University Bonn (#255/06). Certified pathologists with extensive experience in preparation and analysis of breast cancer surgery resectates for diagnostics and research performed pathological staging for the tumor cohort in this study. Tumor histology, grading, and expression assessment of standard clinical biomarkers (ER, PR, HER2, Ki-67) were determined at the time of diagnostic pathological work-up according to the current ASCO/CAP recommendations (Rakha et al., 2014, Histopathology 64, 609-615). Areas of tumor in the surgery resectates were identified macroscopically prior to sample-taking or microscopically in fast frozen section analyses. Part of the tumor was formalin cross-linked, embedded in paraffin, and stained with hematoxylin and eosin and if necessary with standard immunohistochemistry (IHC) procedures as part of standard diagnostics. For mass cytometry analysis, a tissue sample of about 5×5×5 mm (about 0.125 $cm^3$ volume) was taken prior to paraffin embedding, thus the tumor area processed for mass cytometry analysis was spatially separate from the tumor area stained for prognostic and predictive biomarkers. However, the pathologists selected a research sample for this study that was macroscopically representative of the whole tumor based on many years of experience. From the clinical perspective, the presence of DCIS is of less importance for diagnosis than detection of tumor invasiveness, and invasive tumor tissues were chosen as tumor-representative samples for this study. It is likely that DCIS surrounding the tumor was also sampled and possible that some DCIS was present in non-cancerous tissue juxtaposed to the tumor. This might underlie the grouping of some juxta-tumoral tissue samples with their matched tumor. Since the specific tissue areas used in this study could not be examined by frozen section or hematoxylin and eosin because they were dissociated during the mass cytometry workflow, the inventors unfortunately do not know whether and how much DCIS was present in each of the samples. The inventors have an indication based on the pathological histology analysis. It is highly unlikely, however, that extensive areas of DCIS in the non-cancerous juxta-tumoral tissue were overlooked preoperatively, since the patients underwent extensive imaging of the breast before surgery, and no abnormalities were noted. The small differences between the percentages of cells positive for ER, PR, HER2, and Ki-67 as assessed by pathological IHC compared to the mass cytometry analysis are likely caused by usage of differences in antibody clones, in assay sensitivities, and in sampled tumor volumes (mass cytometry, large volume about 0.125 $cm^3$; IHC, small volume). Tumor subtype definitions in this study were as follows: Luminal A ($ER^+$ and/or $PR^+$, $HER2^-$, Ki-$67^+$ <20%), Luminal B ($ER^+$ and/or $PR^+$, $HER2^-$, Ki-$67^+$≥20%), Luminal B-$HER2^+$ ($ER^+$ and/or $PR^+$, $HER2^+$), $HER2^+$ (ER-PR-$HER2^+$), and triple negative (TN; ER-PR-$HER2^-$). Some tumor ecosystems grouped together with juxta-tumoral and mammoplasty samples. These were of Luminal A subtype and low grade, possibly reflecting that the tumor was phenotypically similar to non-cancerous tissue or that the tumor content was particularly low in these samples. Ten patients had received neoadjuvant (NA) chemotherapy prior to sample collection for this study including one of 56 Luminal A, five of 72 Luminal B, two of six Luminal B-HER2*, and two of six TN patients (Table S2). The inventors did not see any significant difference between tumors from NA-treated patients and tumors from untreated patients in terms of cell type frequency, epithelial and immune phenotype frequencies, phenotypic abnormality, or individuality.

Cell Lines

Human mammary epithelial cell lines were obtained from the American Type Culture Collection (ATCC) and cultured according to ATCC recommendations. Cell lines included MCF-10A, MDA-MB-134-VI, MDA-MB-231, MDA-MB-453, SK-BR-3, and ZR-75-1. Fibroblasts were a gift from the laboratory of Prof. Silvio Hemmi at the University of Zurich and were cultured in DMEM medium (Sigma Aldrich) supplemented with 2 mM L-glutamine, 1 mM sodium pyruvate, and 10% fetal bovine serum (FBS). Peripheral blood mononuclear cells (PBMCs) from healthy donors were obtained from the Zurich Blood Transfusion Service and were isolated by histopaque (Sigma Aldrich) density gradient centrifugation.

Tissue Preparation

Following surgical resection, fresh tissue samples were immediately transferred to pre-cooled MACS Tissue Storage Solution (Miltenyi Biotec) and were shipped at 4° C. Tissue processing was completed within 24 hours of collection. For dissociation, the tissue was minced using surgical scalpels and further disintegrated using the Tumor Dissociation Kit, human (Miltenyi Biotech) and the gentleMACS Dissociator (Miltenyi Biotech) according to manufacturer's instructions. The resulting single-cell suspension was filtered sequentially through sterile 70-pm and 40-pm cell strainers. The cell suspension was stained for viability with 25 μM cisplatin (Enzo Life Sciences) in a 1-min pulse before quenching with 10% FBS. Cells were then fixed with 1.6% paraformaldehyde (PFA, Electron Microscopy Sciences) for 10 min at room temperature and stored at −80° C.

Mass-Tag Cellular Barcoding

To minimize inter-sample staining variation, the inventors applied mass-tag barcoding to fixed cells (Zunder et al., 2015, Nat. Protoc. 10, 316-333). A 126-well barcoding scheme composed of unique combinations of four out of nine barcoding metals was used for this study; metals included palladium ($^{105}$Pd, $^{106}$Pd, $^{108}$Pd, $^{110}$Pd, Fluidigm) conjugated to bromoacetamidobenzyl-EDTA (Dojindo) as well as indium ($^{113}$In and $^{115}$In, Fluidigm), yttrium, rhodium, and bismuth ($^{89}$Y, $^{103}$Rh, $^{209}$Bi, Sigma Aldrich) conjugated to maleimido-mono-amide-DOTA (Macrocyclics). The concentrations were adjusted to 20 nM ($^{209}$Bi), 100 nM ($^{105-110}$Pd, $^{115}$In, $^{89}$Y), 200 nM ($^{113}$In), or 2 μM ($^{103}$Rh). Cells were randomly distributed across two 96-well plates, and about 0.3 million cells per well were barcoded using a transient partial permeabilization protocol. Cells were washed once with 0.03% saponin in PBS (Sigma Aldrich) prior to incubation in 200 μl barcoding reagent for 30 min at room temperature. Cells were then washed four times with cell staining medium (CSM, PBS with 0.3% saponin, 0.5% bovine serum albumin (Sigma Aldrich) supplemented with 2 mM EDTA (Stemcell Technologies) and pooled for antibody staining. Two 126-well barcoding plates, with a set of standard samples on each plate, were used for antibody staining with the tumor cell-centric and the immune cell-centric panels.

Antibodies and Antibody Labeling

Target specificity of the antibodies was confirmed in the inventors' laboratory. Antibodies were obtained in carrier/protein-free buffer or were purified using the Magne Protein A or G Beads (Promega) according to manufacturer's instructions. Metal-labeled antibodies were prepared using the Maxpar X8 Multimetal Labeling Kit (Fluidigm) according to manufacturer's instructions. After conjugation, the protein concentration was determined using a Nanodrop (Thermo Scientific), and the metal-labeled antibodies were diluted in Antibody Stabilizer PBS (Candor Bioscience) to a concentration of 200 or 300 μg/ml for long-term storage at 4° C. Optimal concentrations for antibodies were determined by titration, and antibodies were managed using the cloud-based platform AirLab as previously described (Catena et al., 2016, Genome Biol. 17).

Antibody Staining and Cell Volume Quantification

Antibody staining was performed on pooled samples after mass-tag cellular barcoding. The pooled samples were incubated with FcR Blocking Reagent, human (Miltenyi Biotech) for 10 min at 4° C. and then washed once with CSM. For staining with the tumor cell-centric antibody panel, purified rabbit anti-human ERα (Epitomics) was applied at 3 μg/ml for 45 min at 4° C., and then samples were washed twice with CSM. Goat anti-rabbit IgG (Vector Labs) conjugated to $^{165}$Ho was then applied at 0.25 μg/ml for 45 min at 4° C. followed by two washes with CSM. The sample was then stained with 1.5 ml of the antibody panel per ~50 million cells for 45 min at 4° C. followed by three washes with CSM. For mass-based cell detection, cells were stained with 500 μM nucleic acid intercalator iridium ($^{191}$Ir and $^{193}$Ir, Fluidigm) in PBS with 1.6% PFA (Electron Microscopy Sciences) for 1 h at room temperature or overnight at 4° C. Cells were washed once with CSM and once with 0.03% saponin in PBS. For cell volume quantification, cells were stained with 12.5 μg/ml Bis(2,2'-bipyridine)-4'-methyl-4-carboxybipyridine-ruthenium-N-succidimyl ester-bis (hexafluorophosphate) ($^{96}$Ru, $^{98-102}$Ru, $^{104}$Ru, Sigma Aldrich) in 0.1 M sodium hydrogen carbonate (Sigma Aldrich) for 10 min at room temperature as previously described (Rapsomaniki et al., 2018, Nat. Commun. 9.).

Cells were then washed twice with CSM, twice with 0.03% saponin in PBS, and twice with doubly distilled water ($ddH_2O$). For mass cytometry acquisition, cells were diluted to 0.5 million cells/ml in $ddH_2O$ containing 10% EQ™ Four Element Calibration Beads (Fluidigm) and filtered through a 40-μm filter-cap FACS tube. Samples were placed on ice and introduced into the Helios upgraded CyTOF2 (Fluidigm) using the Super Sampler (Victorian Airship) introduction system; data were collected as .fcs files.

Gadolinium Contamination Test

Some patients were scanned by magnetic resonance imaging for medical diagnosis and received a gadolinium-based contrast agent. A small aliquot of each sample was tested for the presence of gadolinium after fixation using mass cytometry. Gadolinium-positive cells were removed from data analysis by gating.

Immunofluorescence Imaging

The inventors selected formalin-fixed paraffin embedded (FFPE) sections of breast cancer resectates for which mass cytometry analysis has been performed on a different region of the same tumor. FFPE sections were stained using the Opal 7-Color IHC Kit (PerkinElmer) according to manufacturer's protocol. Briefly, slides were deparaffinized, rehydrated, and antigen retrieved using Trilogy buffer (Cell-Marque) by autoclaving for 15 min. Slides were treated with 3% $H_2O_2$ for 15 min, washed, and blocked using 4% BSA/PBS/0.1% Triton X-100 (all from Sigma). Primary antibodies and consecutive HRP-conjugated secondary antibodies were diluted in 1% BSA/PBS/0.1% Triton X-100. Primary antibodies were incubated over night at 4° C. and secondary antibodies were incubated for 1 h at room temperature. Slides were then incubated in Amplification diluent containing a tyramide-conjugated fluorophore for 10 min. Prior to the next primary antibody incubation, the slides were heated for 10 min in 10 mM citric acid, pH 6.0 at 95° C. to strip the antibodies of the previous staining round. The protocol was repeated from the blocking step until a total of six markers were co-stained. After the last staining round, the slides were washed, incubated with 0.5 μg/ml 4',6 diamidine-2-phenylindole (DAPI; ThermoFischer) for 5 min, washed again, and mounted using Prolong Diamond medium (ThermoFischer). The following set of markers was analyzed for each sample (indicated in the order of staining): CTLA-4, PD-L1, PD-1, CD68, CD3e, PanK+EpCAM. Slides were scanned using the multispectral imaging system Vectra 3.0 (PerkinElmer), and multispectral images were analyzed using the InForm Cell Analysis software (PerkinElmer). Images were processed in Fiji and contrast was enhanced to improve visibility.

Mass Cytometry Data Preprocessing

Mass cytometry data were concatenated using the .fcs File Concatenation Tool (Cytobank, Inc.), normalized using the MATLAB version of the Normalizer tool (Finck et al., 2013, Cytom. Part A 83 A, 483-494), and debarcoded using the CATALYST R/Bioconductor package (Chevrier et al., 2018, Cell Syst. 6, 612-620.e5). Debarcoded files were compensated for channel crosstalk using single-stained polystyrene beads as previously described (Chevrier et al., 2018, Cell Syst. 6, 612-620.e5). The compensated .fcs files were uploaded to the Cytobank server (Cytobank, Inc.) for manual gating on populations of interest. For FIG. 1, manual gates were set to exclude nonspecific background signal and cisplatin-positive dead cells. The resulting population was exported as .fcs files and loaded into R (R Development Core Team, 2015) for downstream analysis. Sample duplicates that were used to ensure high data quality between two barcoding plates were concatenated for downstream analysis.

Dimensionality Reduction and Clustering

For dimensionality reduction visualizations using the t-SNE algorithm (Van Der Maaten and Hinton, 2008, J. Mach. Learn. Res. 9, 2579-2605), signal intensities (dual counts) per channel were arcsin h-transformed with a cofactor of 5 (counts_transf=a sin h(x/5)). The R t-SNE package for Barnes-Hut implementation was used. For marker expression level visualization on t-SNE plots, the expression was normalized between 0 and 1 to the 99$^{th}$ percentile and the top percentile was set to 1.

Epithelial Cell Selection and Immune Cell Type Selection

To generate an in-depth phenotypic characterization of epithelial and immune cells, the inventors applied PhenoGraph (Levine et al., 2015, Cell 162, 184-197), a state-of-the-art graph based clustering algorithm able to partition high-dimensional data into groups.

Chord Diagram

Pairwise correlations between clusters were visualized as chord diagrams in R using the circlize package (Gu et al., 2014, Bioinformatics 30, 2811-2812). Links are shown for all cluster pairs with p<0.01 using Spearman correlation.

Tumor Grouping

To group the samples based on shared patterns in their ecosystem, the inventors clustered the frequencies per sample of all epithelial and immune clusters. The population frequencies quantify to which extent each sample belongs to the different clusters.

TABLE 1

| Prospectively collected tumors | | | | | |
|---|---|---|---|---|---|
| | Clinical subtype | | | | |
| Receptor status | Luminal A ER+ and/or PR+ Ki-67 < 20% | Luminal B ER+ and/or PR+ Ki-67 ≥ 20% | Luminal B-HER2+ ER+ and/or PR+ HER2+ | HER2+ ER-PR-HER2+ | TN ER-PR-HER2- |
| Total | 56 | 72 | 6 | 1 | 6 |
| Age at surgery [Years] | | | | | |
| <50 | 9 | 9 | 0 | 0 | 3 |
| ≥50 | 47 | 63 | 6 | 1 | 3 |
| Median | 62 | 64 | 66,5 | 61 | 50 |
| Range | 37-93 | 35-87 | 51-88 | 61 | 29-61 |
| Menopausal status | | | | | |
| pre-menopausal | 12 | 17 | 0 | 0 | 3 |
| peri-menopausal | 4 | 1 | 0 | 0 | 0 |
| post-menopausal | 40 | 52 | 6 | 1 | 2 |
| TNM staging | | | | | |
| T1 | 21 | 15 | 2 | 0 | 0 |
| T2 | 32 | 48 | 2 | 1 | 5 |
| T3 | 4 | 4 | 1 | 0 | 1 |
| T4 | 0 | 4 | 1 | 0 | 0 |
| N0 | 32 | 44 | 3 | 1 | 3 |
| N1-N3 | 22 | 26 | 3 | 0 | 2 |
| M0 | 49 | 66 | 5 | 1 | 6 |
| M1 | 3 | 4 | 0 | 0 | 0 |
| Tumor grading | | | | | |
| G1 | 18 | 3 | 0 | 0 | 0 |
| G2 | 35 | 31 | 3 | 0 | 1 |
| G3 | 3 | 38 | 3 | 1 | 5 |
| Neoadjuvant therapy | | | | | |
| Yes | 1 | 5 | 2 | 0 | 2 |
| Previous cancer | | | | | |
| Yes | 9 | 9 | 1 | 1 | 2 |

The invention claimed is:

1. A method of treatment of an estrogen receptor (ER) positive breast cancer in a human subject, the method comprising:

isolating immune cells from a subject;

detecting an expression level of markers presenting on the immune cells selected from the group consisting of PD-1, CTLA-4, CD38, CD45, CD3, CD25, TIM-3, FOXP3, CD4, and CD8;

identifying the subject as having at least one immune cell ratio above a corresponding threshold, and administering to the identified subject a checkpoint modulator agent, wherein the ratio and the threshold are selected from the group consisting of at least 7% of CD45$^+$ immune cells are CD3$^+$CD4$^+$CD25$^+$FOXP3$^+$ regulatory T cells;

at least 7% of CD45$^+$ immune cells are CD3$^+$CD4$^+$CD25$^+$FOXP3$^+$CTLA-4$^+$ regulatory T cells;

at least 3% of CD45$^+$ immune cells are PD-1$^+$CTLA-4$^+$TIM3$^{31}$ CD38$^-$ T cells;

at least 0.1% of CD45$^+$ immune cells are PD-1$^+$CTLA-4$^+$TIM3$^{30}$ CD38$^+$ T cells;

at least 22% of CD4$^+$ T cells are CD3$^+$CD4$^+$CD25$^+$FOXP3$^+$ regulatory T cells;

at least 22% of CD4$^+$ T cells are CD3$^+$CD4$^+$CD25$^+$FOXP3$^+$CTLA-4$^+$ regulatory T cells;

at least 4% of CD45$^+$ immune cells are PD-1$^+$CTLA-4$^+$CD38$^+$CD4$^+$ T cells;

at least 0.4% of CD45$^+$ immune cells are PD-1$^+$CTLA-4$^+$CD38$^+$CD8$^+$ T cells;

at least 12% of CD4$^+$ T cells are PD-1$^+$CTLA-4$^+$CD38$^+$CD4$^+$ T cells; and at least 23% of CD8$^+$ T cells are PD-1$^+$CTLA-4$^+$CD38$^+$CD8$^+$ T cells thereby treating the ER positive breast cancer.

2. The method of claim 1, further comprising administering an anti-estrogen drug.

3. The method of claim 1, wherein the checkpoint modulator agent is selected from the group consisting of:

a. a non-agonist antibody or antibody-like molecule, specifically reactive to any one of the group consisting of CTLA-4, PD-1, PD-L1, PD-L2, LAG-3, TIM-3, BLTA, TIGIT, VISTA or B7/H3; or b. an agonist antibody or antibody-like molecule, specifically reactive to any one of the group consisting of CD137 (4-1BB), CD134 (OX40), CD357 (GITR), CD278 (ICOS), CD27, or CD28.

4. The method according to claim 1, wherein the markers selected from the group consisting of PD-1, CTLA-4, CD38, CD45, CD3, CD25, TIM-3, LAG-3, FOXP3, CD4, and/or CD8 are identified by mass cytometry.

5. The method according to claim 1, wherein the markers selected from the group consisting of PD-1, CTLA-4, CD38, CD45, CD3, CD25, TIM-3, LAG-3, FOXP3, CD4, and CD8 are identified by fluorescence cytometry.

6. The method according to claim 1, wherein at least 9% of CD45$^+$ immune cells are CD3$^+$CD4$^+$CD25$^+$FOXP3$^+$ regulatory T cells.

7. The method according to claim 1, wherein at least 9% of CD45$^+$ immune cells are CD3$^+$CD4$^+$CD25$^+$FOXP3$^+$ CTLA-4$^{30}$ regulatory T cells.

8. The method according to claim 1, wherein at least 5% of CD45$^+$ immune cells are PD-1$^+$CTLA-4$^+$TIM3$^-$CD38$^-$T cells.

9. The method according to claim 1, wherein at least 0.3% of CD45$^+$ immune cells are PD-1$^+$CTLA-4$^+$TIM3$^+$CD38$^+$ T cells.

10. The method according to claim 1, wherein at least 28% of CD4$^+$ T cells are CD3$^+$CD4$^+$CD25$^+$FOXP3$^+$ regulatory T cells.

11. The method according to claim 1, wherein at least 28% of CD4$^+$ T cells are CD3$^+$CD4$^+$CD25$^+$FOXP3$^+$CTLA-4$^+$ regulatory T cells.

12. The method according to claim 1, wherein at least 6% of CD45$^+$ immune cells are PD-1$^+$CTLA-4$^+$CD38$^+$CD4$^+$ T cells.

13. The method according to claim 1, wherein at least 0.6% of CD45$^+$ immune cells are PD-1$^+$CTLA-4$^+$CD38$^+$ CD8$^+$ T cells.

14. The method according to claim 1, wherein at least 16% of CD4$^+$ T cells are PD-1$^+$CTLA-4$^+$CD38$^+$CD4$^+$ T cells.

15. The method according to claim 1, wherein at least 27% of CD8$^+$ T cells are PD-1$^+$CTLA-4$^+$CD38$^+$CD8$^+$ T cells.

16. The method of claim 1, wherein the subject is administered a checkpoint modulator agent if at least three of the expression levels of the markers are above their respective threshold.

17. The method of claim 1, wherein the subject is administered a checkpoint modulator agent if at least four of the expression levels of the markers are above their respective threshold.

18. A method of treatment of an estrogen receptor (ER) positive breast cancer, the method comprising:

isolating immune cells from a subject;

detecting an expression level of markers presenting on the immune cells selected from the group consisting of PD-1, CTLA-4, CD38, CD45, CD3, CD25, TIM-3, FOXP3, CD4, and CD8;

detecting a ratio of the markers on the immune cells;

identifying a subject having the ratio above a threshold, and administering to the identified subject a checkpoint modulator agent, wherein the ratio and the threshold are selected from the group consisting of at least 7% of CD45$^+$ immune cells are CD3$^+$CD4$^+$CD25$^+$ FOXP3$^+$ regulatory T cells;

at least 7% of CD45$^+$ immune cells are CD3$^+$CD4$^+$CD25$^+$ FOXP3$^+$CTLA-4$^+$ regulatory T cells;

at least 3% of CD45$^+$ immune cells are PD-1$^{+CTLA\text{-}}$4$^+$ TIM3$^-$CD38$^-$ T cells;

at least 0.1% of CD45$^+$ immune cells are PD-1$^+$CTLA-4$^+$TIM3$^+$CD38$^+$ T cells;

at least 22% of CD4$^+$ T cells are CD3$^+$CD4$^+$CD25$^+$ FOXP3$^+$ regulatory T cells;

at least 22% of CD4$^+$ T cells are CD3$^+$CD4$^+$CD25$^+$ FOXP3$^+$CTLA-4$^+$ regulatory T cells;

at least 4% of CD45$^+$ immune cells are PD-1$^+$CTLA-4$^+$ CD38$^+$CD4$^+$ T cells;

at least 0.4% of CD45$^+$ immune cells are PD-1$^+$CTLA-4$^+$CD38$^+$CD8$^+$ T cells;

at least 12% of CD4$^+$ T cells are PD-1$^+$CTLA-4$^+$CD38$^+$ CD4$^+$ T cells; and at least 23% of CD8$^+$ T cells are PD-1$^+$CTLA-4$^+$CD38$^+$ CD8$^+$ T cells. thereby treating the ER positive breast cancer.

* * * * *